US011033310B2

United States Patent
Cook et al.

(10) Patent No.: US 11,033,310 B2
(45) Date of Patent: Jun. 15, 2021

(54) MAGNETIC SCREW AND PLATE APPARATUS

(71) Applicant: Gomboc, LLC, Metairie, LA (US)

(72) Inventors: Stephen D. Cook, Metairie, LA (US); Michael C. Harrison, Metairie, LA (US); Liam P. Nolan, New Orleans, LA (US)

(73) Assignee: Gomboc, LLC, Metairie, LA (US)

( * ) Notice: Subject to any disclaimer, the term of this patent is extended or adjusted under 35 U.S.C. 154(b) by 0 days.

(21) Appl. No.: 15/677,822

(22) Filed: Aug. 15, 2017

(65) Prior Publication Data

US 2019/0053838 A1 Feb. 21, 2019

Related U.S. Application Data

(60) Provisional application No. 62/545,572, filed on Aug. 15, 2017.

(51) Int. Cl.
*A61B 17/84* (2006.01)
*A61B 17/86* (2006.01)
*A61B 17/70* (2006.01)
*A61B 17/80* (2006.01)
*A61B 17/00* (2006.01)
*A61B 90/92* (2016.01)

(52) U.S. Cl.
CPC ........ *A61B 17/866* (2013.01); *A61B 17/7059* (2013.01); *A61B 17/8014* (2013.01); *A61B 17/8042* (2013.01); *A61B 17/864* (2013.01); *A61B 17/8625* (2013.01); *A61B 17/8023* (2013.01); *A61B 90/92* (2016.02); *A61B 2017/00876* (2013.01)

(58) Field of Classification Search
CPC ........ A61B 17/7058–7059; A61B 17/80–8095
See application file for complete search history.

(56) References Cited

U.S. PATENT DOCUMENTS

| 4,024,588 | A | 5/1977 | Janssen et al. |
| 5,098,435 | A | 3/1992 | Stednitz et al. |
| 5,536,127 | A | 7/1996 | Pennig |
| 5,544,993 | A | 8/1996 | Harle |
| 5,595,563 | A | 1/1997 | Moisdon |
| 5,735,853 | A | 4/1998 | Olerud |
| 5,879,386 | A * | 3/1999 | Jore .......... A61F 2/38 623/16.11 |
| 6,030,162 | A | 2/2000 | Huebner |

(Continued)

OTHER PUBLICATIONS

International Search Report and Written Opinion by the International Searching Authority in PCT Application No. PCT/US2018/046790, dated Apr. 1, 2020.

(Continued)

*Primary Examiner* — Eduardo C Robert
*Assistant Examiner* — Steven J Cotroneo
(74) *Attorney, Agent, or Firm* — Grimes & Yvon LLP

(57) ABSTRACT

A bone screw comprising a shaft, in which the shaft comprises a bore that is configured to fit a magnet. In addition, a bone plate comprising apertures that can fit the bone screw. The bone plate may be fastened to bone using the bone screws, and the bone screws may be oriented to generate attractive or repulsive forces.

35 Claims, 19 Drawing Sheets

(56) References Cited

U.S. PATENT DOCUMENTS

| | | | |
|---|---|---|---|
| 6,599,321 B2* | 7/2003 | Hyde, Jr. | A61B 17/68 623/18.12 |
| 6,641,583 B2 | 11/2003 | Shluzas et al. | |
| 7,857,836 B2 | 12/2010 | Huebner et al. | |
| 8,029,570 B2* | 10/2011 | Barnes | A61B 17/58 623/18.12 |
| 9,011,505 B2 | 4/2015 | Prandi et al. | |
| 9,161,793 B2 | 10/2015 | Huebner | |
| 10,016,220 B2* | 7/2018 | Culbert | A61B 17/7016 |
| 2002/0032484 A1 | 3/2002 | Hyde | |
| 2003/0078583 A1 | 4/2003 | Biedermann et al. | |
| 2004/0059423 A1 | 3/2004 | Barnes et al. | |
| 2005/0258694 A1* | 11/2005 | Leininger | H02K 7/183 310/156.32 |
| 2006/0100626 A1* | 5/2006 | Rathbun | A61B 17/1728 606/86 B |
| 2006/0247650 A1* | 11/2006 | Yerby | A61B 17/025 606/90 |
| 2007/0100457 A1 | 5/2007 | Hyde | |
| 2007/0123879 A1* | 5/2007 | Songer | A61B 17/8033 606/288 |
| 2007/0179493 A1* | 8/2007 | Kim | A61B 17/7025 606/33 |
| 2007/0185489 A1* | 8/2007 | Abdou | A61B 17/7059 606/255 |
| 2008/0015578 A1* | 1/2008 | Erickson | A61L 31/022 606/281 |
| 2008/0132960 A1 | 6/2008 | Weaver et al. | |
| 2008/0306324 A1 | 12/2008 | Bonutti et al. | |
| 2009/0048618 A1 | 2/2009 | Harrison et al. | |
| 2009/0054951 A1* | 2/2009 | Leuthardt | A61N 1/205 607/46 |
| 2009/0082810 A1* | 3/2009 | Bhatnagar | A61B 17/7002 606/250 |
| 2009/0099404 A1* | 4/2009 | Kraus | A61N 2/02 600/13 |
| 2009/0318976 A1 | 12/2009 | Gabriel et al. | |
| 2010/0030337 A1 | 2/2010 | Ani et al. | |
| 2010/0211120 A1* | 8/2010 | Bonutti | A61B 17/0401 606/86 R |
| 2010/0228252 A1 | 9/2010 | Courtney et al. | |
| 2011/0098523 A1* | 4/2011 | Kraus | A61N 2/02 600/13 |
| 2011/0257754 A1 | 10/2011 | Fleischmann | |
| 2011/0319943 A1* | 12/2011 | Donahoe | A61B 17/7059 606/290 |
| 2012/0245641 A1* | 9/2012 | Mekhail | A61B 17/7059 606/279 |
| 2013/0165980 A1 | 6/2013 | Cook et al. | |
| 2014/0025122 A1 | 1/2014 | Cook et al. | |
| 2014/0081121 A1* | 3/2014 | Wilhelm | A61B 17/72 600/409 |
| 2014/0135851 A1 | 5/2014 | Cook et al. | |
| 2014/0188178 A1* | 7/2014 | Juchno | A61B 17/7007 606/292 |
| 2015/0022333 A1* | 1/2015 | Jim | A45C 13/24 340/434 |
| 2017/0007300 A1* | 1/2017 | Garrido | A61B 17/7059 |
| 2017/0231768 A1 | 8/2017 | Gross | |
| 2018/0014838 A1 | 1/2018 | Ning | |
| 2019/0021776 A1* | 1/2019 | Archbold | A61B 17/8625 |
| 2019/0053864 A1 | 2/2019 | Cook et al. | |
| 2019/0053908 A1 | 2/2019 | Cook et al. | |

OTHER PUBLICATIONS

U.S. Appl. No. 13/707,250, filed Dec. 6, 2012, 2013/0165980, U.S. Pat. No. 9,579,135.

U.S. Appl. No. 14/075,896, filed Nov. 8, 2013, 2014/0135851, U.S. Pat. No. 9,968,391.

U.S. Appl. No. 15/835,802, filed Dec. 8, 2017, 2019/0053864, U.S. Pat. No. 10,555,787.

U.S. Appl. No. 16/005,641, filed Jun. 11, 2018, 2019/0053908, (pending).

* cited by examiner

MAGNETIC SCREW AND PLATE APPARATUS

CROSS-REFERENCE TO RELATED APPLICATIONS

This application claims the benefit of U.S. Provisional Application Ser. No. 62/545,572, filed on Aug. 15, 2017, which is hereby incorporated by reference in its entirety.

BACKGROUND OF THE INVENTION

In vertebrates (including mammals such as humans), bones and connective tissues such as cartilage can break, fracture, or otherwise become damaged due to injury, age, heredity, or combinations thereof. This is particularly true for cartilage and components of the intervertebral disc that can degenerate, resulting in pain and pressure on the spinal cord. Prior apparatuses and methods for fixation or fusion of bones and joints to promote healing, relieve pain, and/or reduce future injury are generally known, but many are insufficient to provide proper stability or otherwise aid in healing or treating the bones and connective tissues involved.

SUMMARY OF INVENTION

The present invention relates to devices and methods for use with bone and/or connective tissue repair or treatment.

An aspect of the invention relates to a bone screw. In embodiments of the invention, the bone screw comprises a shaft comprising (i) an upper section, a lower section, and a middle section between the upper section and the lower section, in which the shaft comprises a circular cross-section; (ii) an outer wall surface, in which a plurality of threads is disposed along at least a portion of the outer wall surface; and (iii) a bore defining an inner wall surface. The bone screw also comprises a magnet configured to fit within the bore.

In embodiments of the invention, the bore comprises a general cylindrical shape. In some embodiments, the magnet comprises a general cylindrical shape as well. In certain embodiments, the bore comprises a general cylindrical shape containing a flattened side. In some embodiments, the magnet comprises a general cylindrical shape containing a flattened side.

In embodiments of the invention, the lower section of the shaft is attached to the middle section. In some embodiments, the lower section is hermetically sealed to the middle section. In certain embodiments, the lower section is laser welded to the middle section.

In embodiments of the invention, the magnet is adhered to at least a portion of the inner wall surface. In some embodiments, the magnet is adhered to at least a portion of the inner wall surface using surgical adhesive. In certain embodiments, the surgical adhesive comprises a medical grade epoxy.

In embodiments of the invention, the upper section of the shaft comprises an end surface that is configured to receive a driver. In some embodiments, the end surface of the upper section contains a mark that identifies the polarity of the magnet.

In embodiments of the invention, the lower section comprises a general conical shape.

In embodiments of the invention, the shaft comprises a metal alloy. In certain embodiments, the metal alloy comprises titanium, cobalt chromium, stainless steel, or a combination thereof.

In certain embodiments of the invention, the shaft comprises a length of about 5 to about 100 mm. In some embodiments, the length is about 10 to about 80 mm.

In embodiments of the invention, the shaft comprises a diameter of about 2 to about 12 mm. In some embodiments, the diameter is about 3 to about 10 mm.

Another aspect of the invention relates to a bone plate. In embodiments of the invention, the bone plate comprises a first end section, a second end section, a middle section between the first end section and the second end section, a first surface and a second surface. The first end section comprises at least one aperture, in which the at least one aperture of the first end section is generally circular. The second end section comprises at least one aperture, in which the at least one aperture of the second end section is generally an elongated slot. The at least one aperture of the first end section and the at least one aperture of the second section are each configured to receive a bone screw, such as a bone screw as described above.

In embodiments of the invention, the first surface comprises a contouring profile configured to the contouring profile of at least a portion of a vertebra, such as the vertebral body of the vertebra. In some embodiments, the first surface comprises a contouring profile configured to the contouring profile of at least a portion of the vertebral body of two or more adjacent vertebrae. In certain embodiments, the vertebrae are cervical vertebrae. In other embodiments, the vertebrae are lumbar or thoracic vertebrae.

In embodiments of the invention, the at least one aperture of the first end section comprises a diameter of about 2 to about 12 mm.

In embodiments of the invention, the at least one aperture of the second end section comprises a length of about 2.5 to about 15 mm. In some embodiments, the at least one aperture of the second end section comprises a width of about 2 to about 12 mm.

In embodiments of the invention, the width of the first end section and the second end section is greater than the width of the middle section.

In embodiments of the invention, two apertures are in the first end section and two apertures are in the second end section.

In embodiments of the invention, the bone plate further comprises one or more apertures for receiving a locking tab. In some embodiments, the one or more apertures for receiving a locking tab are in the middle section of the plate.

In embodiments of the invention, the plate comprises a metal alloy, polymer, a composite of polymers and fibers, or a combination thereof. In some embodiments, the metal alloy comprises titanium, cobalt chromium, stainless steel, or a combination thereof. In certain embodiments, the polymer comprises polyetheretherketone, polyurethane, or a combination thereof. In further embodiments, the composite comprises carbon fiber reinforced polyetheretherketone.

An aspect of the invention relates to an apparatus that comprises the bone plate as described above and at least two bone screws as described above.

An aspect of the invention relates to a method of stabilizing a fused intervertebral joint between a first vertebra and a second vertebra. The method comprises fastening a bone plate as described above via two or more bone screws as described above to the first vertebra and the second vertebra, wherein the plate bridges the fused intervertebral joint and at least one bone screw is inserted into each of the first vertebra and the second vertebra.

In some embodiments, the bone screws are inserted through the apertures of the plate to fasten the plate to the first vertebra and to the second vertebra, in which the bone screw(s) inserted through the one or more apertures of the first end section fastens the first end section to the first vertebra, and the bone screw(s) inserted though the one or more apertures of the second end section fastens the second end to the second vertebra. In certain embodiments, the bone screws are oriented to direct the polarity of the magnet in the bone screws such that an attractive magnetic force between the bone screw(s) inserted through the one or more apertures of the first end section and the bone screw(s) inserted though the one or more apertures of the second end section.

An aspect of the invention relates to a method of stabilizing fused intervertebral joints between three or more vertebrae. The method comprises fastening a bone plate as described above via three or more bone screws as described above to each of the three or more vertebrae, wherein the plate bridges each fused intervertebral joint between the three or more vertebrae, and at least one bone screw is inserted into each of vertebrae.

An aspect of the invention relates to a method of preventing or reducing deterioration of a nonfused intervertebral joint that is superior or inferior to a fused intervertebral joint. The method comprises inserting one or more bone screws into a first vertebra and one or more bone screws into a second vertebra that form the nonfused intervertebral joint. The first vertebra may also form a fused intervertebral joint with an adjacent vertebra. In certain embodiments, the bone screws are oriented to direct the polarity of the magnet in the bone screws such that a repulsive magnetic force is generated between the one or more bone screws inserted into the first vertebra and the one or more bone screws inserted into the second vertebra.

BRIEF DESCRIPTION OF THE DRAWING FIGURES

The present disclosure will be further explained with reference to the attached drawing figures, wherein like structures are referred to by like numerals throughout the several views. The drawing figures shown are not necessarily to scale, with emphasis instead generally being placed upon illustrating the principles of the present disclosure, and some features may be exaggerated to show details of particular components. In addition, any measurements, specifications and the like shown in the drawing figures, or described below, are intended to be illustrative, and not restrictive. Therefore, specific structural and functional details disclosed herein are not to be interpreted as limiting, but merely as a representative basis for teaching one skilled in the art to variously employ the bone screw, plate, plate-and-screw apparatus, and methods thereof.

FIG. 2A is a cross-sectional side view of a bone screw, and FIG. 2B is an exploded view of a bone screw.

FIG. 3A is a top view of a bone screw, and FIG. 3B is a cross-sectional bottom view of a bone screw.

FIG. 5A is a side view of a bone plate, FIG. 5B is a cross-sectional end view of a bone plate, and FIG. 5C is a cross-sectional end view of a bone plate.

FIG. 8A is a side view of a bone plate, and FIG. 8B is a cross-sectional side view of a bone plate.

FIG. 9A is a top view of a bone plate with bone screws, and FIG. 9B is a perspective view of a bone plate with bone screws.

FIG. 11A is a top view of a bone plate with bone screws, and FIG. 11B is a side view of a bone plate with bone screws.

FIG. 12A is a top view of a locking tab, and FIG. 12B is a side view of a locking tab.

Figure 13A:
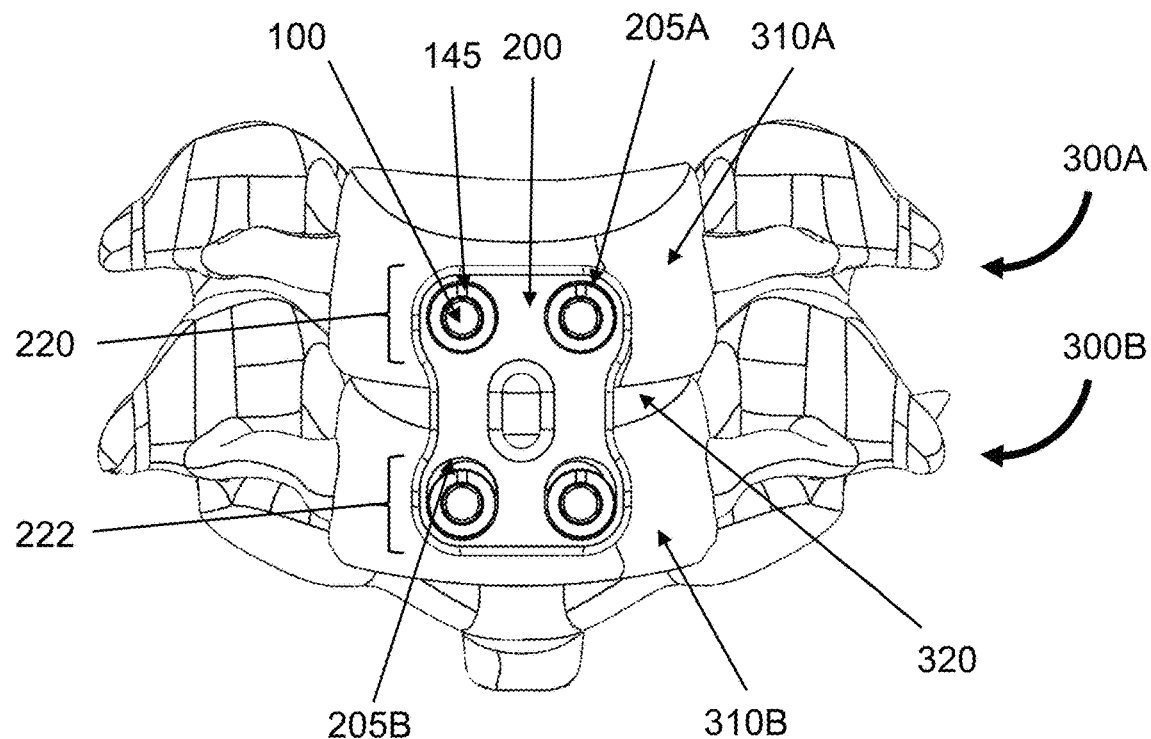
Figure 13B:
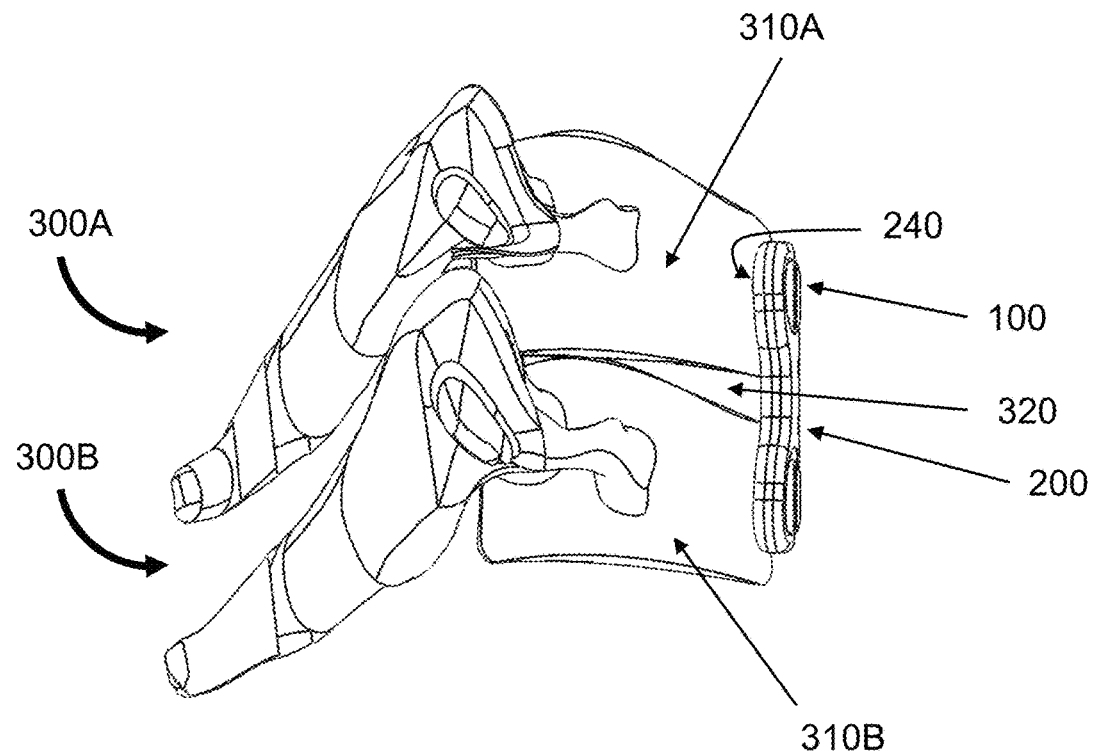

FIGS. 13A and 13B are different views of a bone plate fastened via bone screws to vertebrae of a fused intervertebral joint according to embodiments of the invention. FIG. 13A is a coronal plane view of a bone plate fastened via bone screws to vertebrae of a fused intervertebral joint, and FIG. 13B is a sagittal plane view of a bone plate fastened via bone screws to vertebrae of a fused intervertebral joint.

Figure 14A:
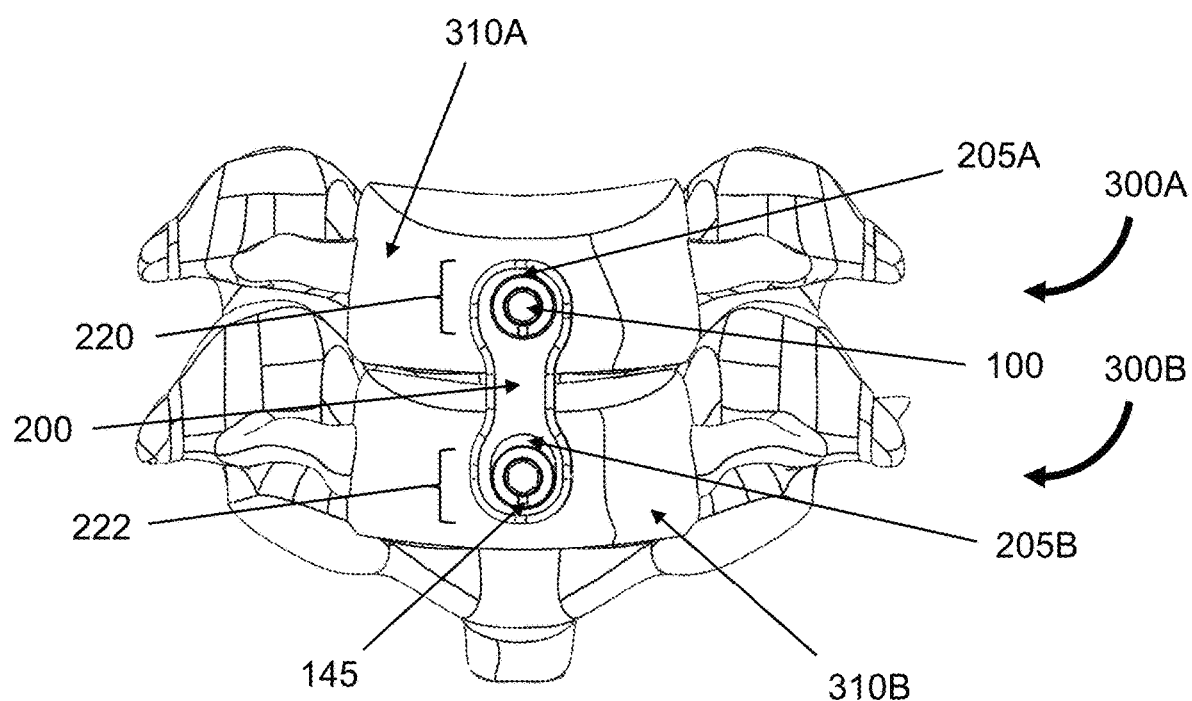
Figure 14B:
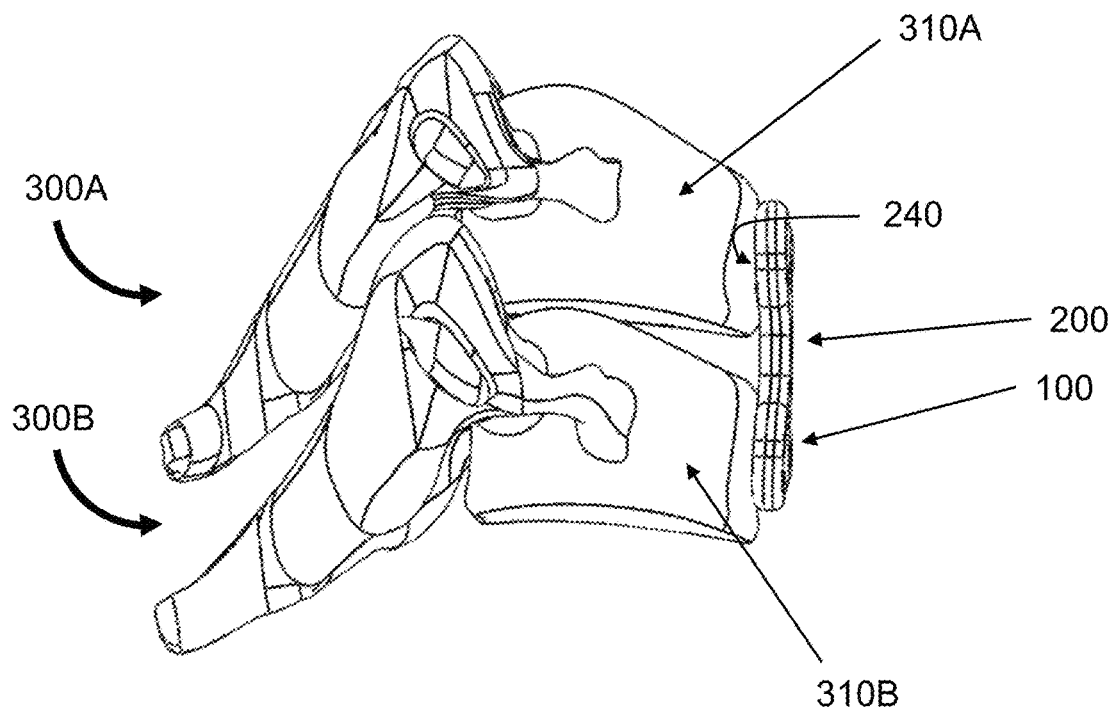

FIGS. 14A and 14B are different views of a bone plate fastened via bone screws to vertebrae of a fused intervertebral joint according to embodiments of the invention. FIG. 14A is a coronal plane view of a bone plate fastened via bone screws to vertebrae of a fused intervertebral joint, and FIG. 14B is a sagittal plane view of a bone plate fastened via bone screws to vertebrae of a fused intervertebral joint.

Figure 15:
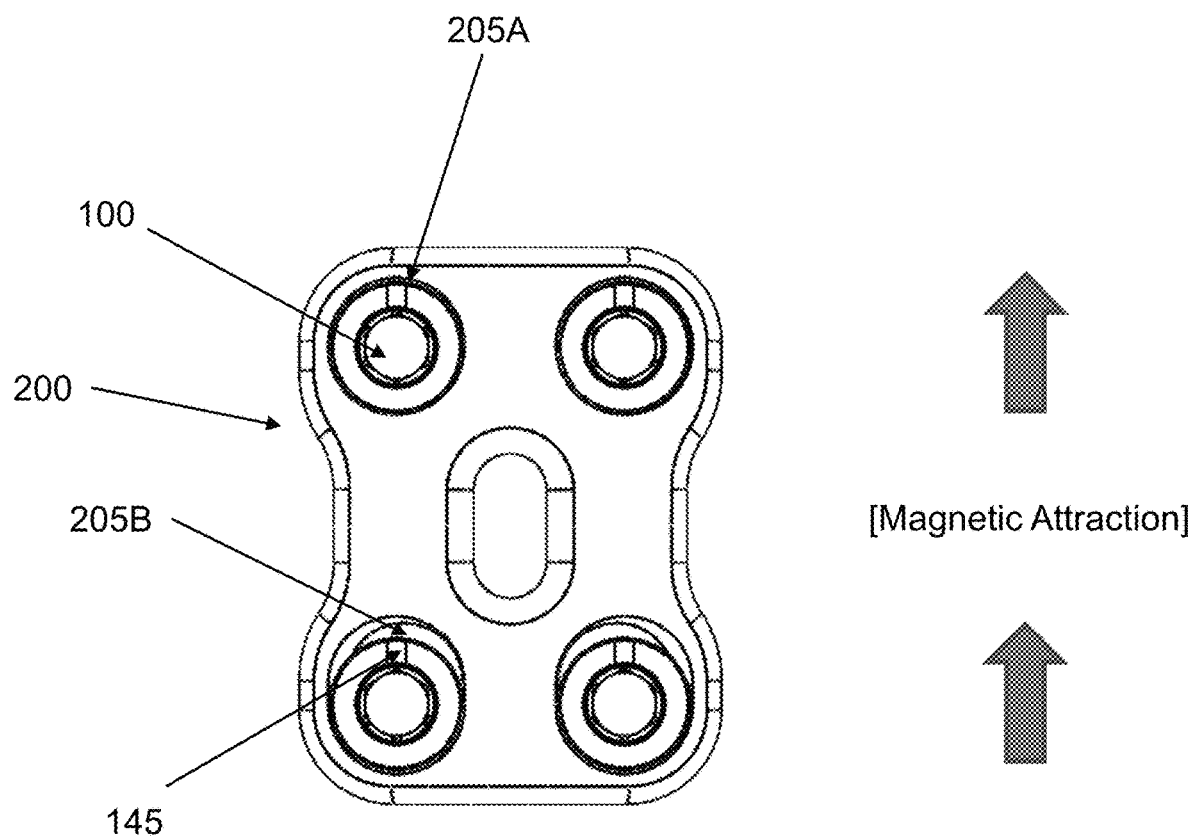

FIG. 15 is a top view of a bone plate with bone screws and the direction of the magnetic north poles of the bone screws according to embodiments of the present invention.

Figure 16A:
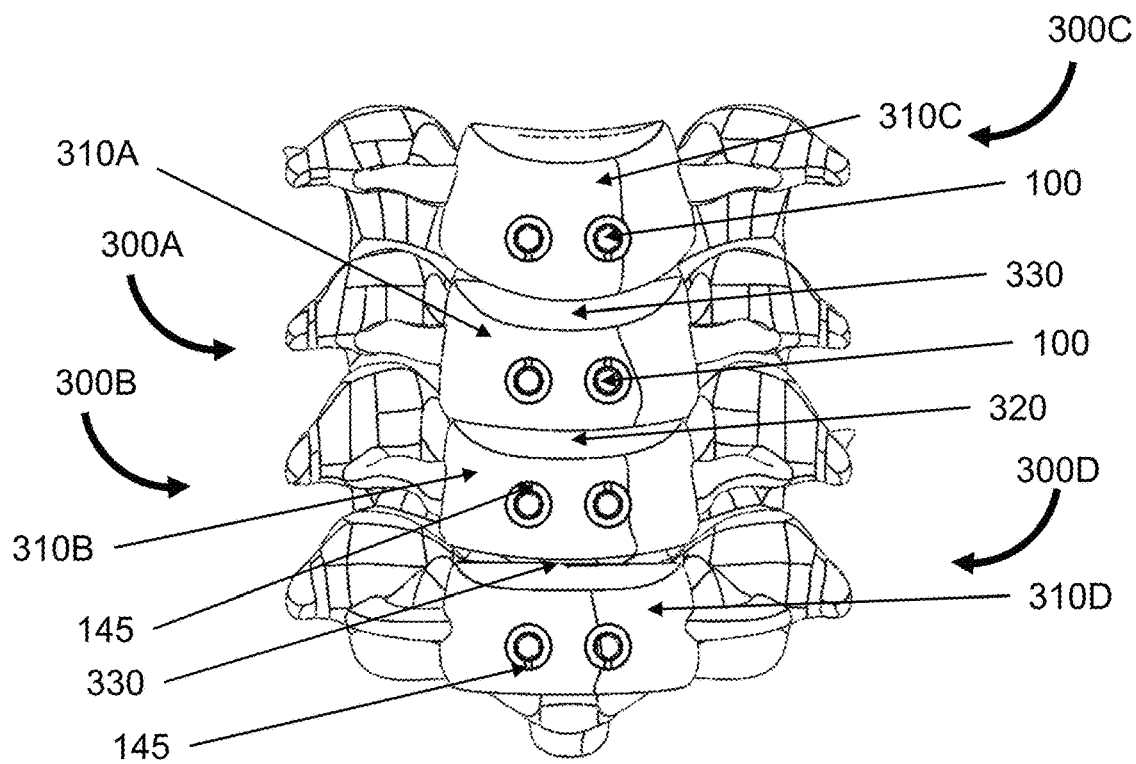
Figure 16B:
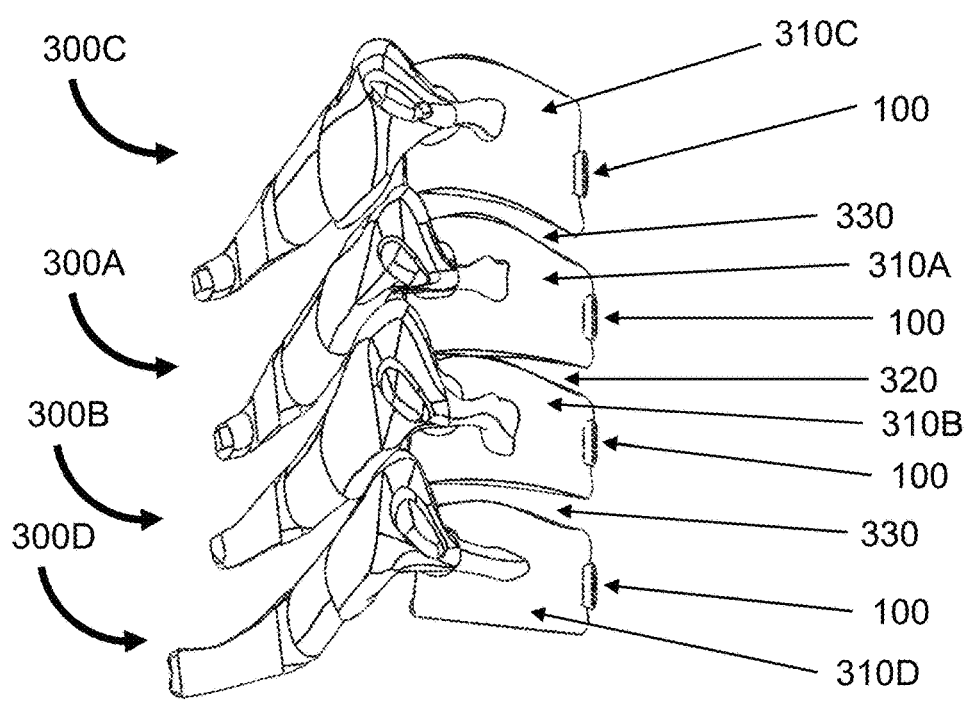

FIGS. 16A and 16B are different views of bone screws inserted into vertebrae of a fused intervertebral joint and additional screws inserted into adjacent vertebrae, according to embodiments of the invention. FIG. 16A is a coronal plane view of bone screws inserted into vertebrae of a fused intervertebral joint and additional screws inserted into adjacent vertebrae, and FIG. 16B is a sagittal plane view of bone screws inserted into vertebrae of a fused intervertebral joint and additional screws inserted into adjacent vertebrae.

Figure 17:
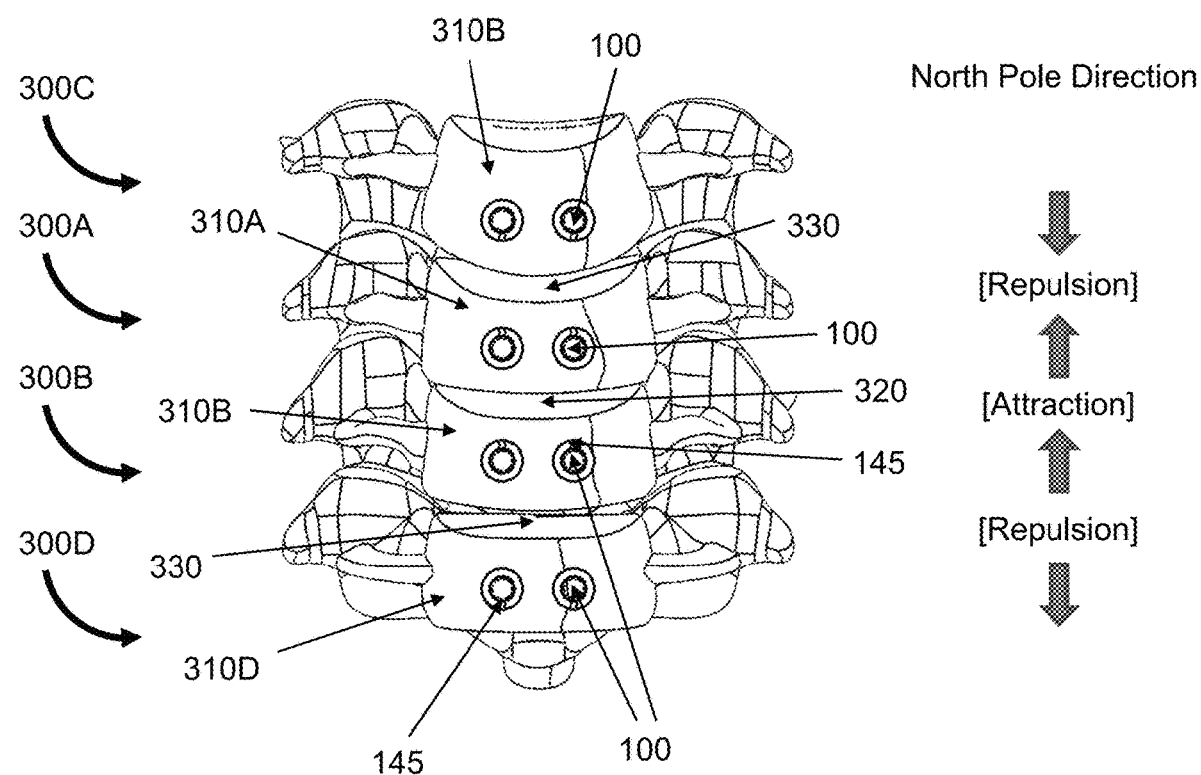

FIG. 17 is a coronal plane view of bone screws inserted into vertebrae of a fused intervertebral joint and additional screws inserted into adjacent vertebrae, and the direction of the magnetic north poles of the bone screws according to embodiments of the present invention.

Figure 18A:
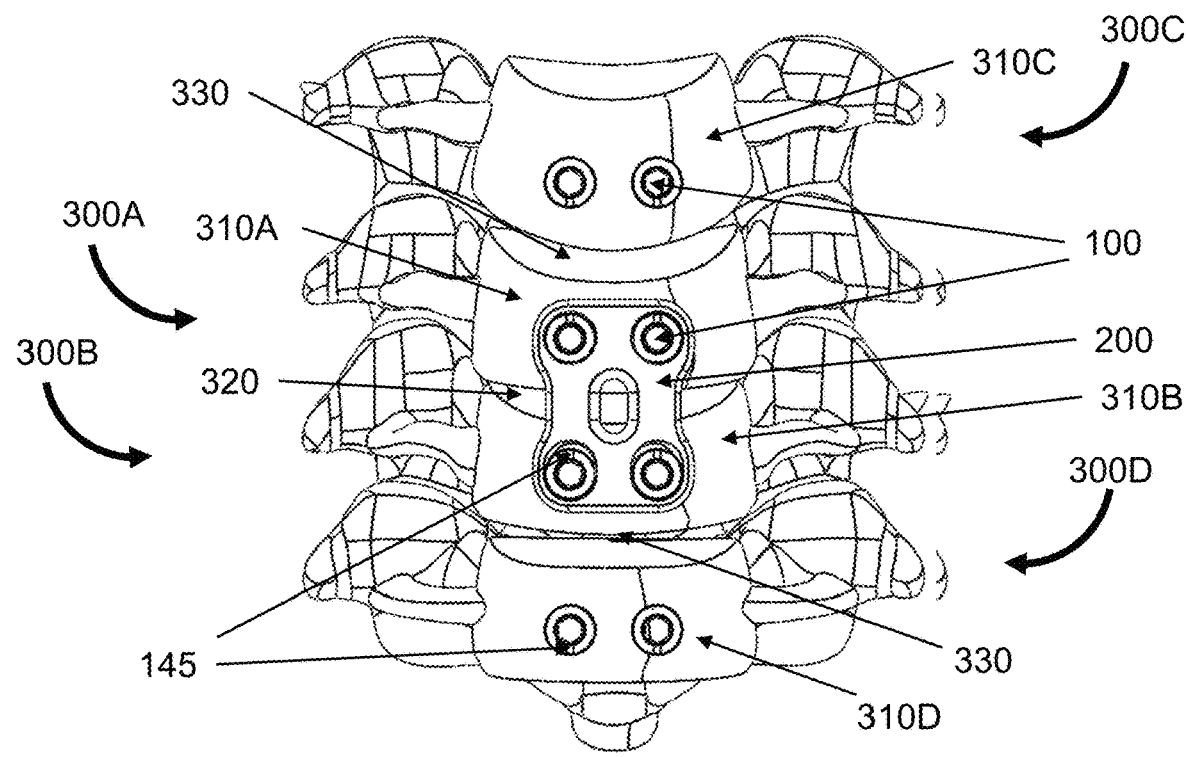
Figure 18B:
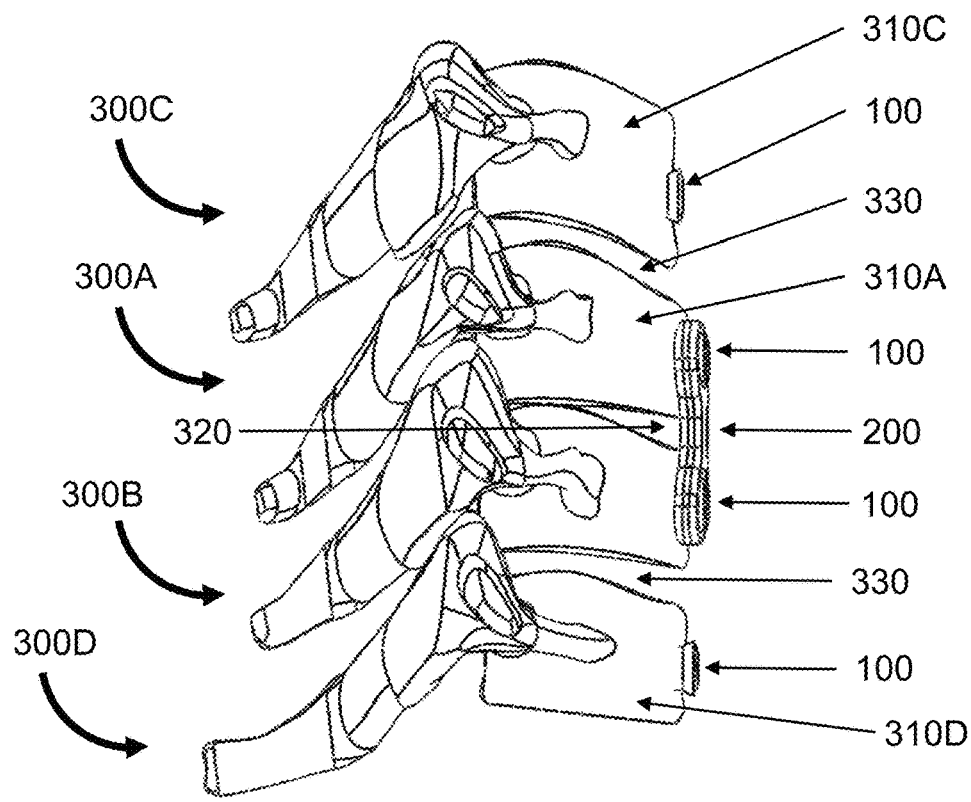

FIGS. 18A and 18B are different views of a bone plate fastened via bone screws to vertebrae of a fused intervertebral joint and additional bone screws inserted into adjacent vertebrae, according to embodiments of the invention. FIG. 18A is a coronal plane view of a bone plate fastened via bone screws to vertebrae of a fused intervertebral joint and additional bone screws inserted into adjacent vertebrae, and FIG. 18B is a sagittal plane view of a bone plate fastened via bone screws to vertebrae of a fused intervertebral joint and additional bone screws inserted into adjacent vertebrae.

Figure 19:
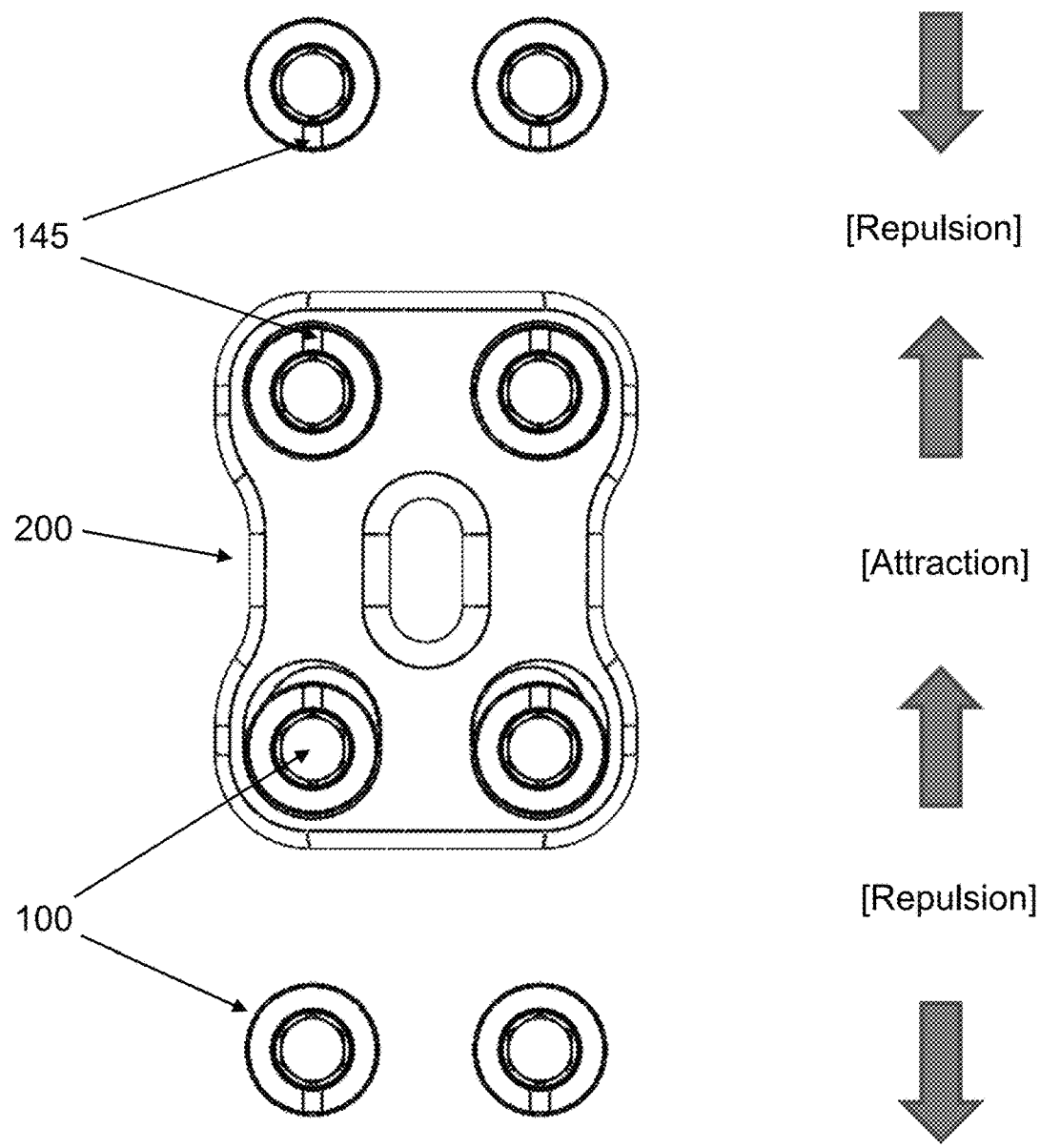

FIG. 19 is a top view of a bone plate with bone screws and additional bone screws, and the direction of the magnetic north poles of the bone screws according to embodiments of the present invention.

DETAILED DESCRIPTION OF THE INVENTION

The present invention relates to a bone screw, plate, plate-and-screw apparatus, and methods thereof.

The bone screws of the present invention comprise a magnet, which generates a polarity. Upon insertion into bone, bone screws can be oriented such that their respective polarities create attractive or repulsive forces between the bone screws. Thus, if a bone screw is inserted into each of two adjacent bones, or into each of two different portions of the same bone, each bone screw can be oriented such that its polarity generates an attractive force between the bone screws that will pull the adjacent bones or the portions of the same bone towards each other; alternatively, each bone screw can be oriented such that its polarity generates a repulsive force between the bone screws that will push the adjacent bones or the portions of the same bone away from each other.

The bone screws of the invention can be used with a plate that can extend across adjacent bones or portions of the same bone. The plate in combination with the screws can be used to stabilize the adjacent bones, or portions of the same bone. As an example, the plate and bone screws can provide stability and compression to two or more adjacent vertebrae while a surgically-induced fusion process occurs.

In some embodiments, the bone plate and one or more bone screws may form an "apparatus" or a "magnetic plate system."

Bone Screws

With reference to FIGS. 1, 2A, 2B, 3A, and 3B, in certain embodiments, bone screw 100 may comprise a shaft 101 having an upper section 105, a middle section 110, and a lower section 115. The shaft 101 may comprise a cross-section that is generally circular.

The shaft 101 may comprise an outer wall 120, onto which there are a plurality of threads 122. The threads 122 may have a pitch, depth, and shape that are known in the art for threads of orthopedic screws, including cortical and cancellous screws. For example, the threads may have any shape as known in the art for drilling into bone, including but not limited to V-thread, buttress thread, reverse buttress, and square thread.

The upper section 105 of the shaft 101 may also be considered as the head of the screw 100. The top surface 107 of the upper section 105 may comprise a drive 140 that is configured for insertion of a driver, such as 2.5 mm tapered hex driver. The drive 140 may also be configured for insertion of other types of drivers, for instance, Philips-head drivers or flat-head drivers.

The shaft 101 may comprise an inner wall surface 125 that is a result of, or is defined by, a bore 130. The bore 130 may be located generally throughout the entire middle section 110 of the shaft 101. A magnet 135 may be housed in the bore 130, and may be entirely encased within the shaft 101, including by the outer wall 120 and by the lower section 115. In certain embodiments, the bore 130 may be generally cylindrical in shape, and therefore the magnet 135 in the bore 130 also may be generally cylindrical in shape. Other shapes are also envisioned for the magnet. For example, the magnet may be ring-shaped, i.e., the magnet itself may comprise a bore through its center along the long axis of the magnet.

The magnet 135 may be prevented from rotating inside the bore 130. In some embodiments, the bore 130 may be generally cylindrical in shape but with at least one flattened side 150, and consequently the magnet 135 in the bore 130 also may be generally cylindrical in shape, but with a flattened side 137. In other embodiments, the bore 130 may be generally cylindrical in shape but may have more than one flattened sides, and the magnet 135 in the bore 130 may also be generally cylindrical in shape but may have more than one flattened sides (not shown). Alternatively, the magnet 135 may be prevented from rotating inside the bore 130 by gluing the magnet 135 to one or more portions of the inner wall surface 125 of the shaft 101. For example, the magnet may be glued in place with a surgical adhesive such as medical grade epoxy. As yet another alternative, the magnet 135 may be tapered to generate a press fit within the bore 130 of the shaft 101 (not shown).

The magnet 135 may comprise materials known in the art. For example, the magnet 135 may be iron-based, nickel-based, cobalt-based, or an alloy of rare-earth metals. In certain embodiments, the magnet 135 may be a rare-earth magnet, which generally has strong attraction and repulsion forces and have high retentive capacity and resistance to demagnification.

The magnet 135 may be magnetized in the radial or axial direction. In some embodiments, the orientation, i.e., the direction of the pole magnetization, of the magnet 135 inside of the bore 130 may be indicated by a mark 145 on the top surface 107 of the upper section 105 of the screw 100. The mark 145 may be a different color or shade than the color of rest of the upper section 105 of the screw 100, e.g., a dark-colored mark; in such a case, the mark 145 may be created, for instance, using laser-etching. The mark 145 may also be a physical feature on the top surface 107 of the upper section 105 of the screw 100, such as a notch or a raised groove.

The shaft 101 may be fabricated with a metal alloy known in the art for orthopedic applications, for example, titanium, cobalt chromium, or stainless steel. In certain embodiments, the upper section 105 and the middle section 110 of the shaft 101 may be fabricated as one continuous component 117. In some embodiments, the lower section 115 may be fabricated as a separate component that is attached to the continuous component 117. The attachment of the lower section 115 to the continuous component 117 may create a hermetically sealed environment within the bore 130 of the shaft. In certain embodiments, the lower section 115 is laser-welded to the continuous component 117.

The physical dimensions of the bone screw 100 are generally consistent with the dimensions of screws for insertion into bone that are known in the art. For example, the length 160 may be about 8 to about 100 mm. The outer diameter 165 may vary depending on whether the screw 100 is being used for insertion into the vertebral body of a cervical vertebra or a lumbar vertebra; for example, the outer diameter 165 may be about 3.5 to about 5 mm for cervical applications, and about 4.5 to about 9.5 for lumbar applications. In some embodiments, the outer diameter 165 may taper at an angle (not shown) of, for instance, about 1 degree or about 10 degrees towards the lower section 115 of the shaft 101. The inner diameter 170 may also taper at an angle (not shown) of, for example, about 1 degree or about 10 degrees towards the lower section 115 of the shaft 101.

Bone Plate

With reference to FIGS. 4, 5A-5C, 6, 7, 8A, and 8B, in certain embodiments, bone plate 200 may comprise a first end section 220, a middle section second 221, and a second end section 222. The bone plate 200 also may comprise a first axis 210 and a second axis 211.

Figure 7:
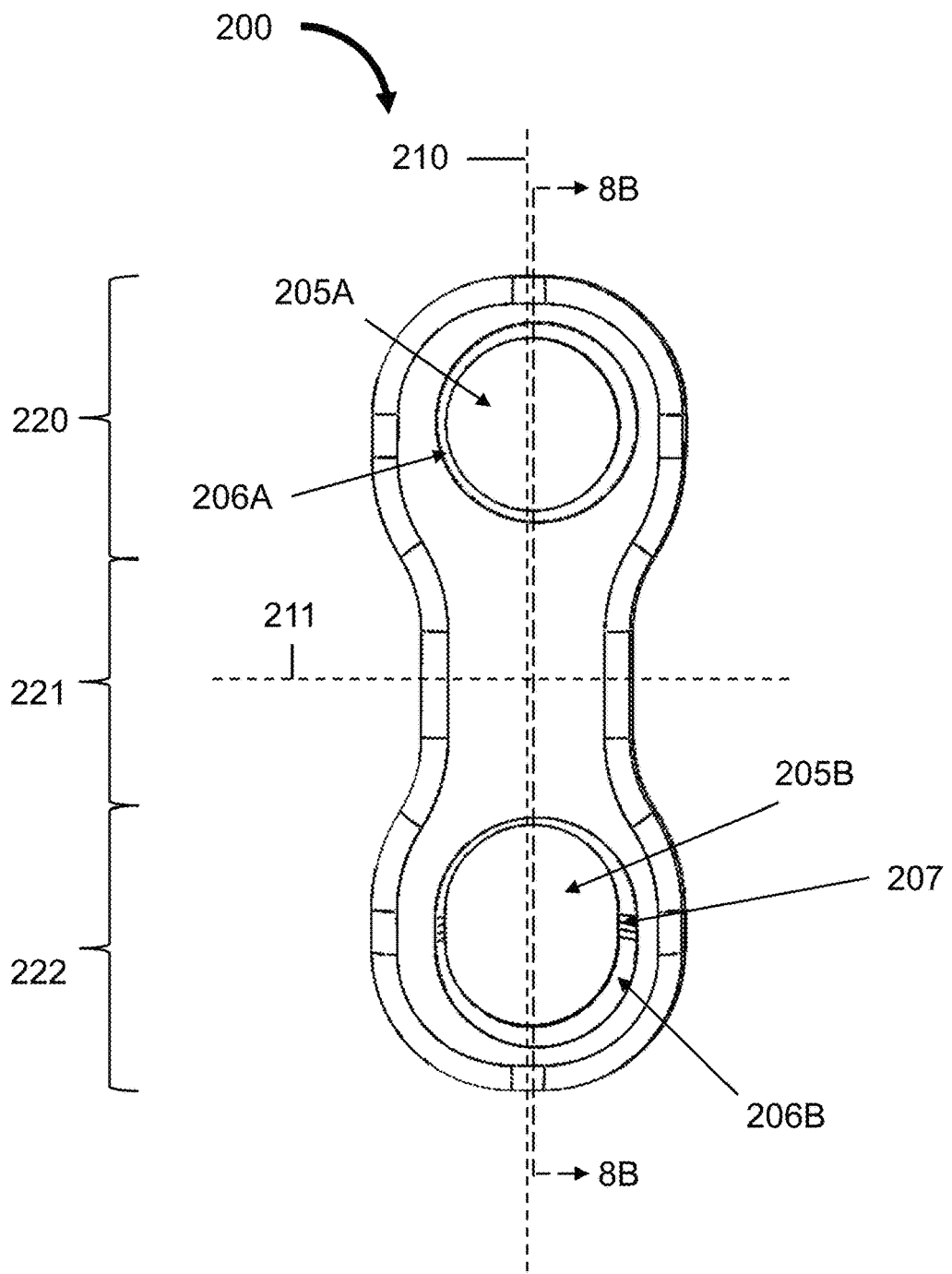
FIG. 7 is a top view of a bone plate according to embodiments of the present invention.
Figure 8A:
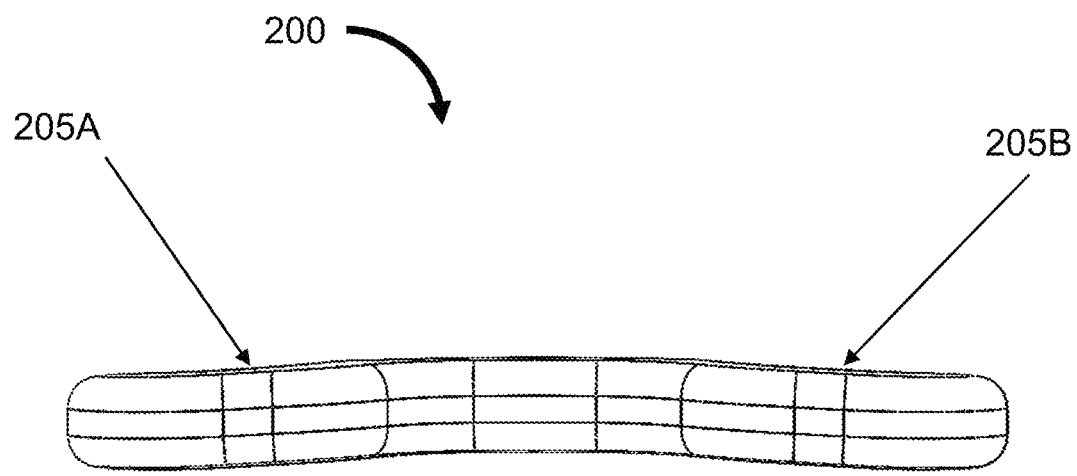
FIGS. 8A and 8B are different views of a bone plate according to embodiments of the present invention.
Figure 8B:
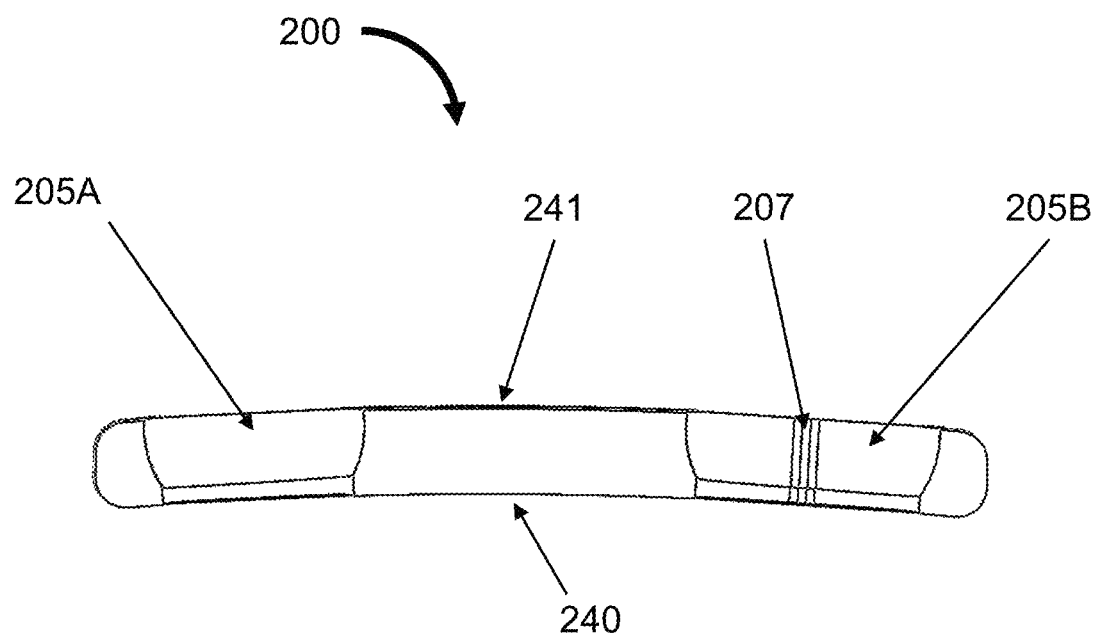
Figure 9A:
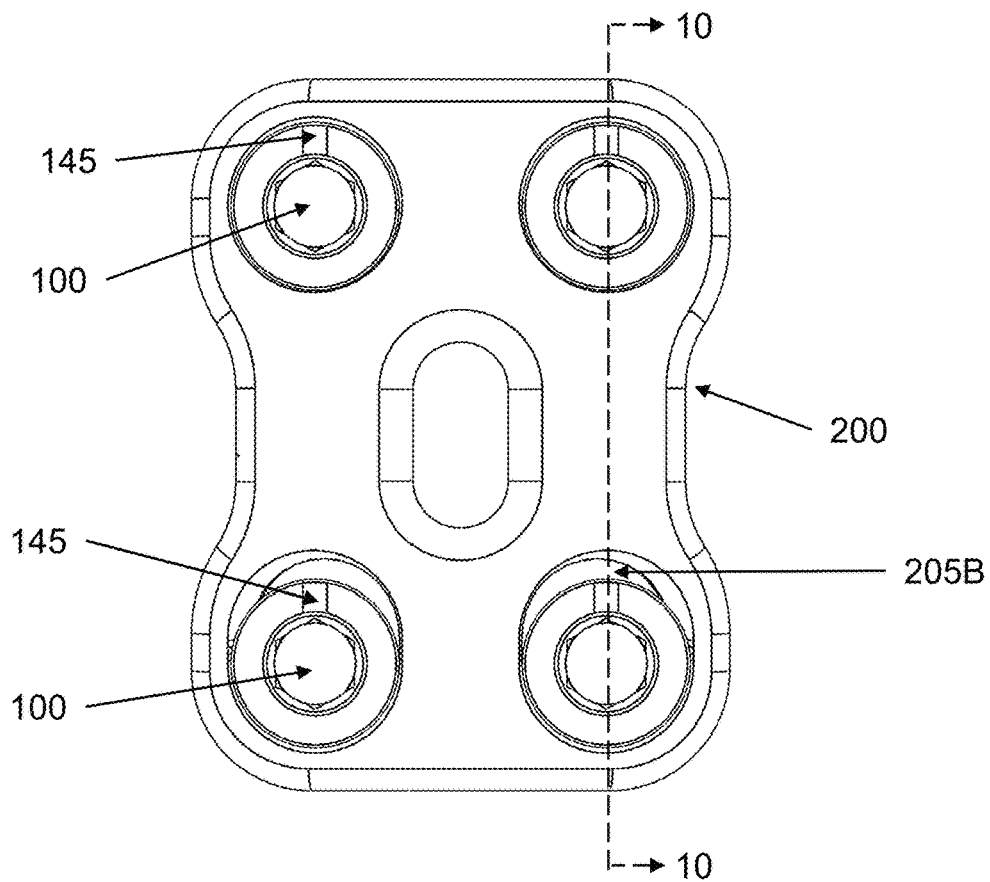
FIGS. 9A and 9B are different views of a bone plate with bone screws according to embodiments of the present invention.
Figure 9B:
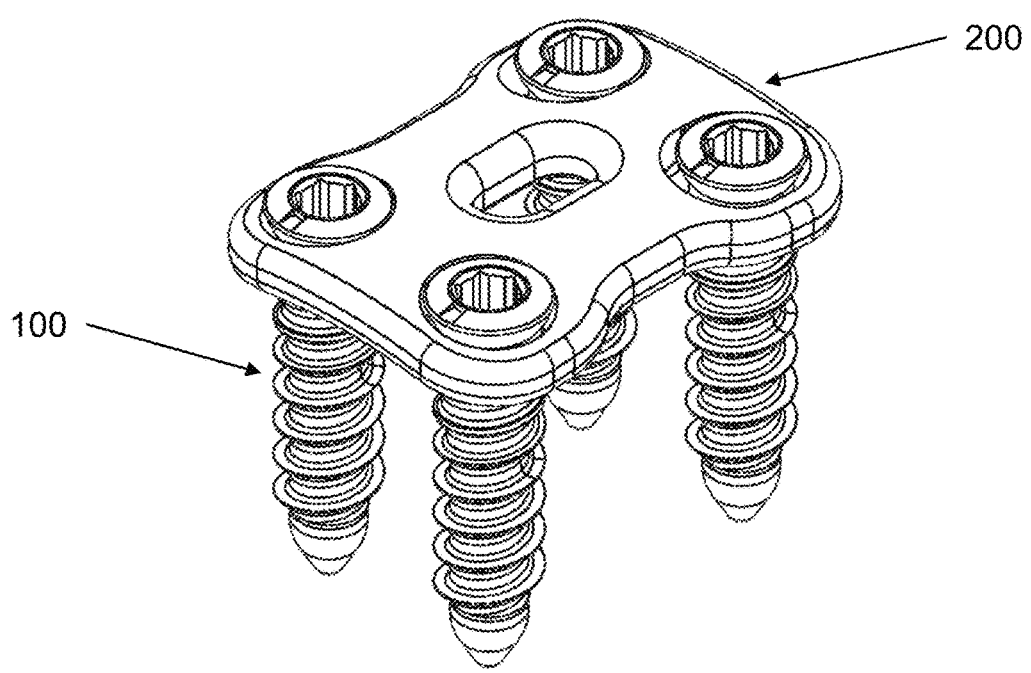
Figure 10:
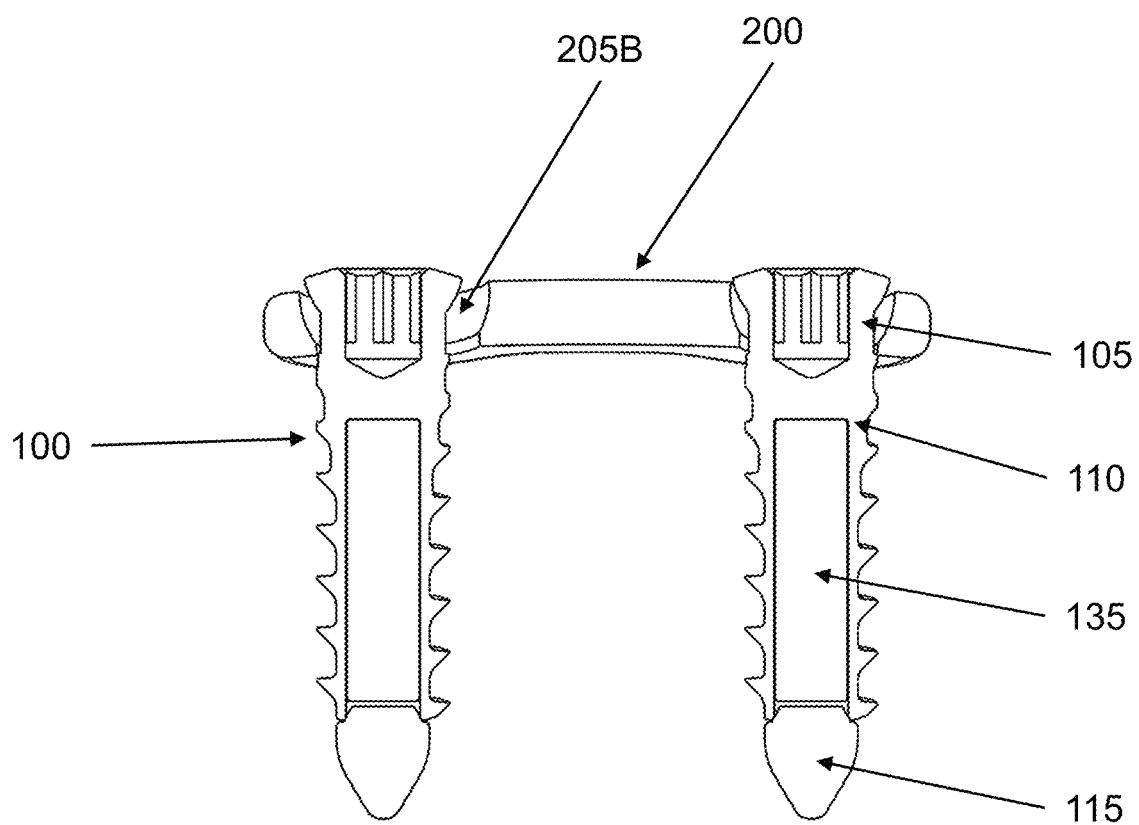
FIG. 10 is a cross-sectional side view of a bone plate with bone screws according to embodiments of the present invention.
Figure 11A:
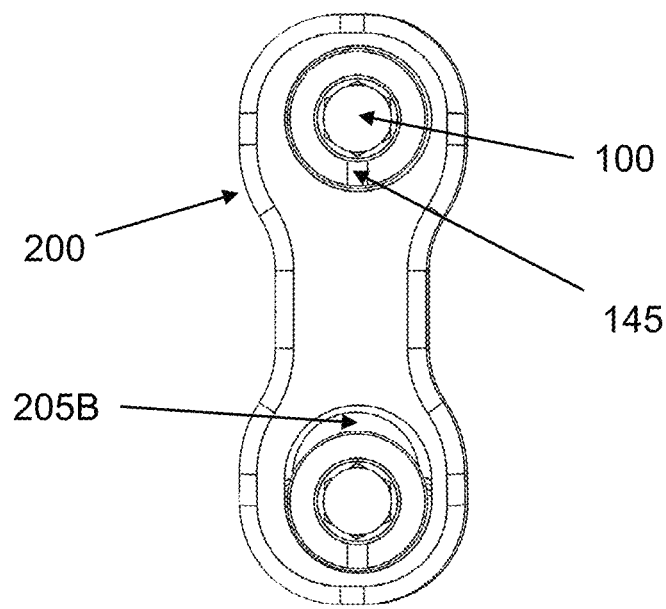
FIGS. 11A and 11B are different views of a bone plate with bone screws according to embodiments of the present invention.
Figure 11B:
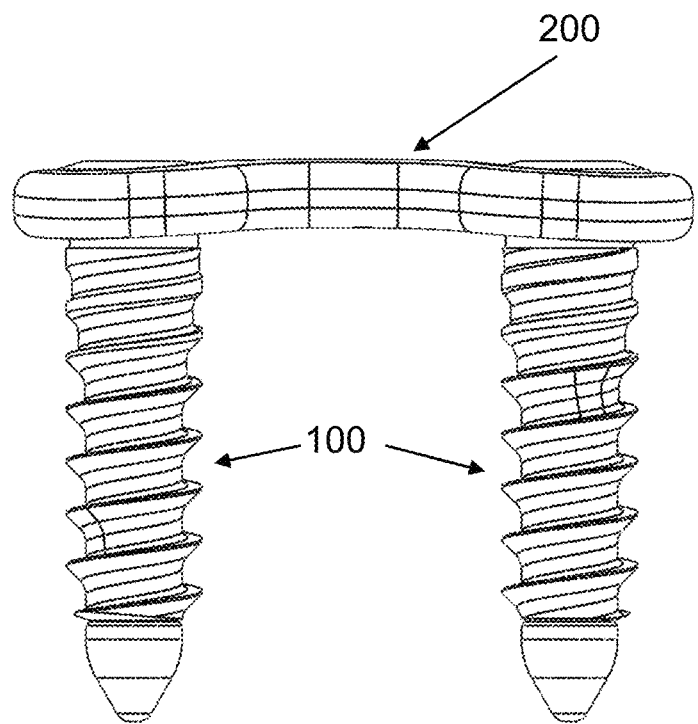

The first end section 220 may comprise at least one aperture 205A; for instance, the first end section 221 may have one aperture 205A (as shown in FIGS. 7, 8A, and 8B), two apertures 205A (as shown in FIGS. 4, 5A-5C, and 6), or more than two apertures 205A (not shown). Each additional aperture 205A is located along the second axis 211 of the plate 200. Apertures 205A of the first end section 220 are generally circular and comprise an inner surface 206A.

The second end section 222 may comprise at least one aperture 205B; for instance, the second end section 222 may have one aperture 205B (as shown in FIGS. 7, 8A, and 8B), two apertures 205B (as shown in FIGS. 4, 5A-5C, and 6), or more than two apertures 205B (not shown). Each additional aperture 205B is located along the second axis 211 of the plate 200. In certain embodiments, the number of apertures 205A in the first section 220 may be the same as the number of apertures 205B in the second end section 222.

The shape of aperture 205B may comprise an elongated slot, i.e., has ends comprising circular segments and a middle therebetween comprising straight segments that are parallel to each other, such that the aperture 205B is longer in the direction of the first axis 210 of the plate 200 as compared to the direction of the second axis 211 of the plate 200. The aperture 205B may comprise an inner surface 206B that, in some embodiments, features a marking 207 indicating that the aperture is in the shape of an elongated slot (i.e., that it is not circular). In certain embodiments, the marking 207 may be on a straight segment of the aperture 205B.

In certain embodiments, aperture 205B in the second end section 222 may be circular. In such embodiments, the bone plate 200 may comprise a means to decrease its length 250, such as a means in which the bone plate 200 can collapse in itself or compress (not shown). For example, the first end section 220 and the second end section 222 may be capable of moving towards each other via a first portion of the plate 200 that slides into a second portion of the plate 200. The first portion, for instance, may be tongue-like in shape, and can slide into the second portion that may comprise a groove or slot. Means to decrease the length 250 of the bone plate 200 are demonstrated by Medtronic's Atlantis Translational® Anterior Cervical Plate, DePuy Synthes's Swift Anterior Cervical Plate, Globulus Medical's Assure Anterior Cervical Plate, K2M's Pyrenees® Translational Cervical Plate System, and NuVasive's Helix Anterior Cervical Plates; and are disclosed in U.S. Pat. Nos. 6,306,136, 6,322,562, and 7,666,185, which are herein incorporated by reference in their entirety.

The middle section 221 may comprise an opening 215 that reduces the weight and amount of material necessary to manufacture the plate 200. Opening 215 may also be used to hold the plate 200 in place while it is fastened to bone. In some embodiments, opening 215 comprises a fillet 216 around the opening 215. The opening may be of any shape, including circular, elongated slot, oval, rectangular, square, triangular, and the like.

Figure 1:
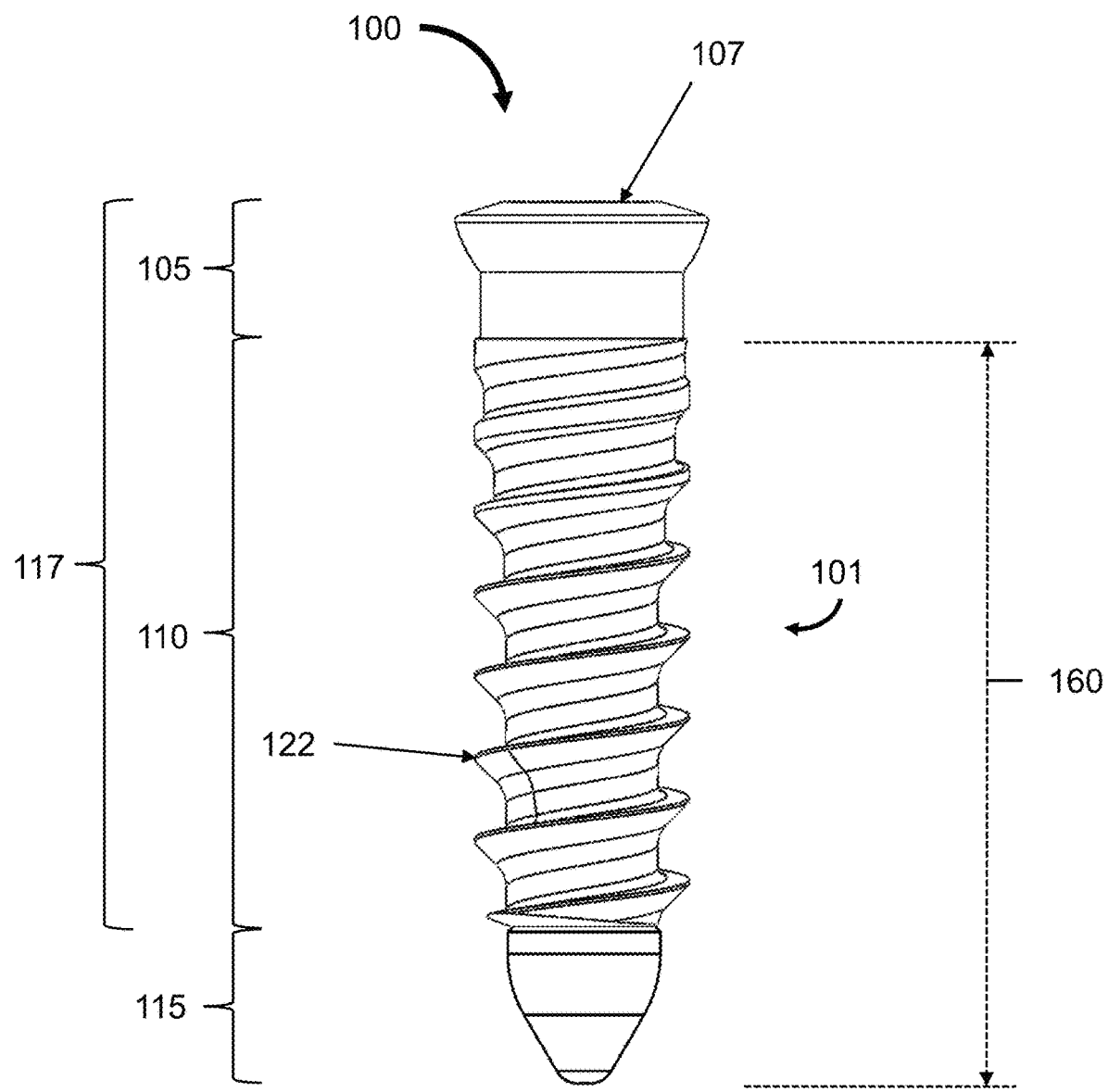
FIG. 1 is a side view of a bone screw according to embodiments of the present invention.
Figures 2A, 2B:
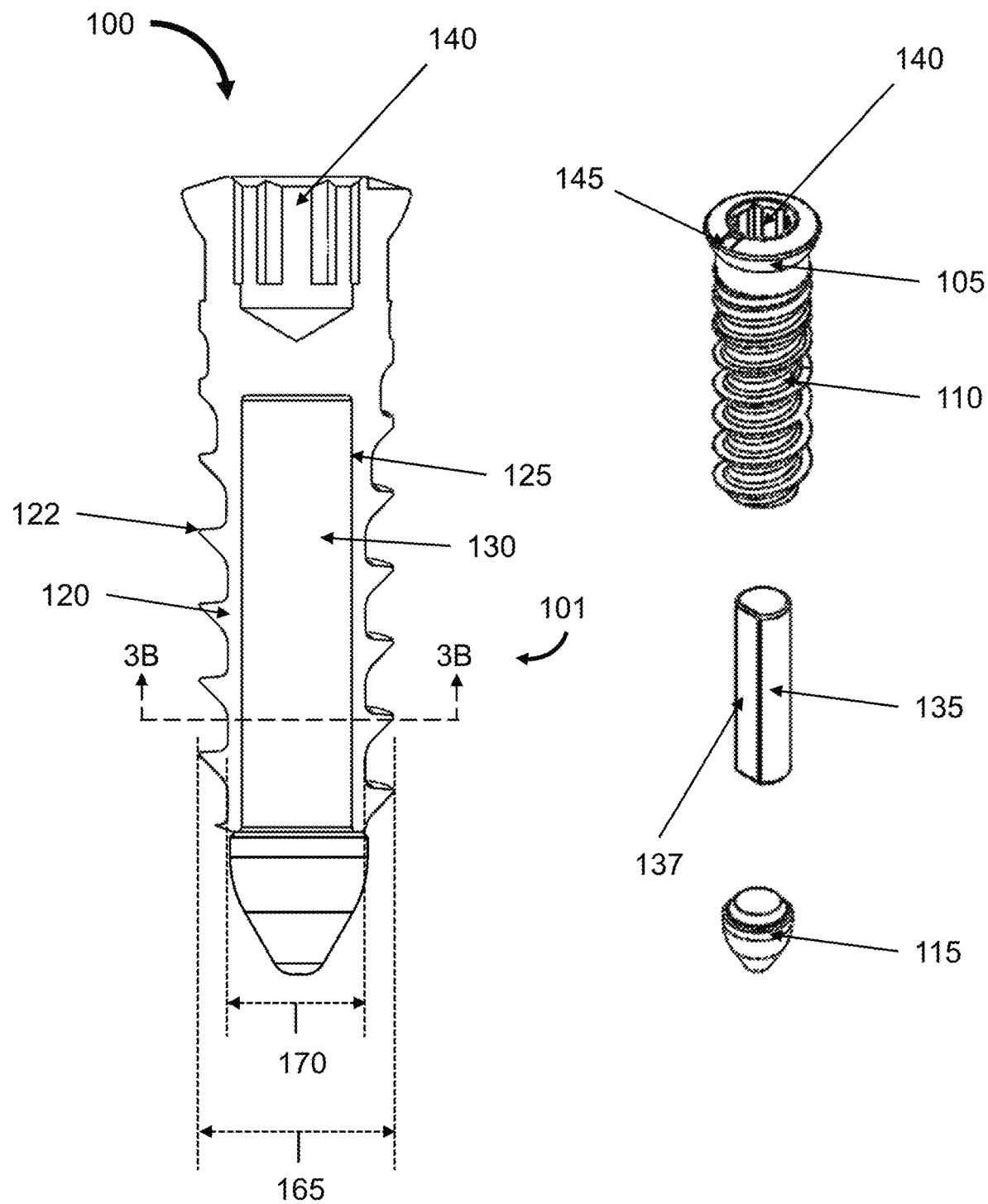
FIGS. 2A and 2B are different views of a bone screw according to embodiments of the present invention.
Figure 3A:
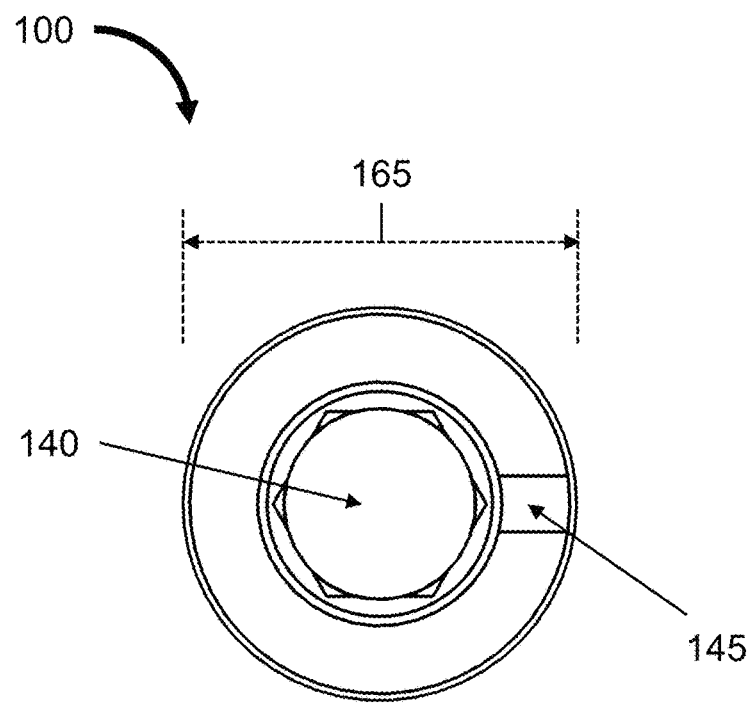
FIGS. 3A and 3B are different views of a bone screw according to embodiments of the present invention.
Figure 3B:
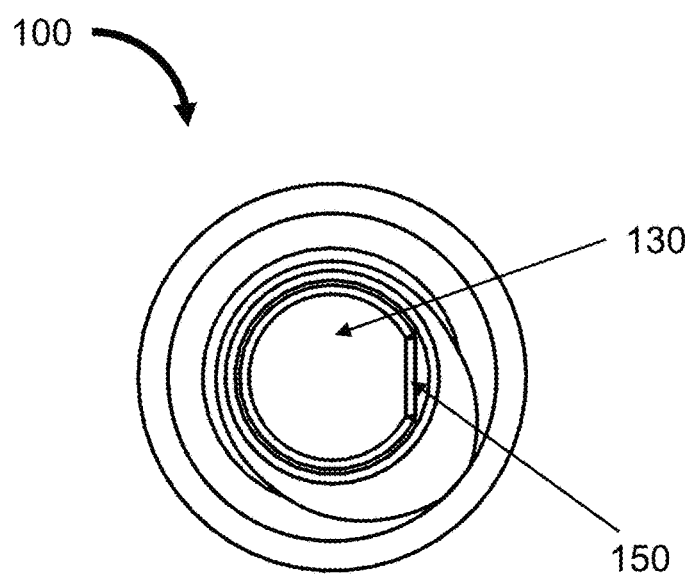
Figure 4:
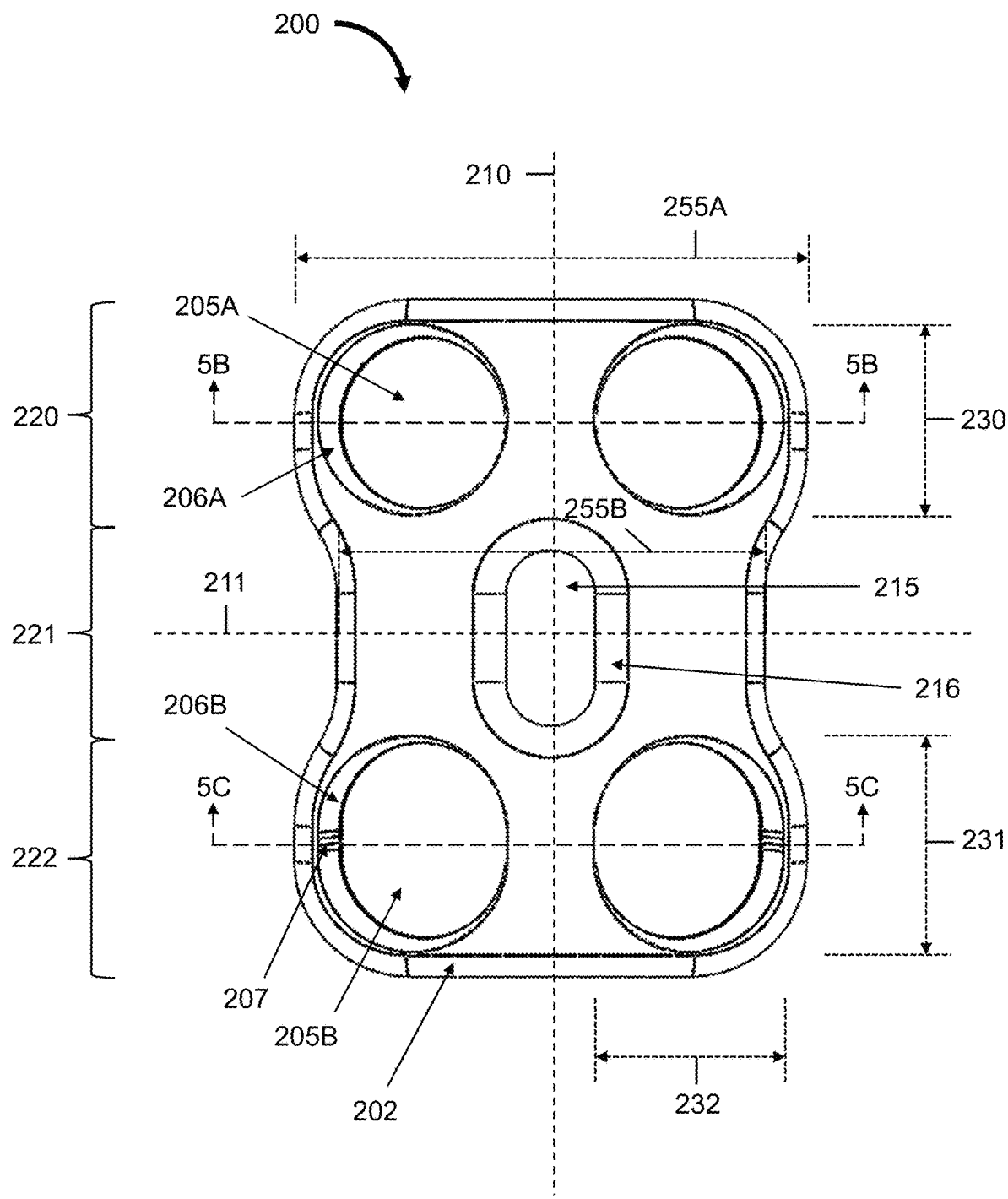
FIG. 4 is a top view of a bone plate according to embodiments of the present invention.
Figure 5A:
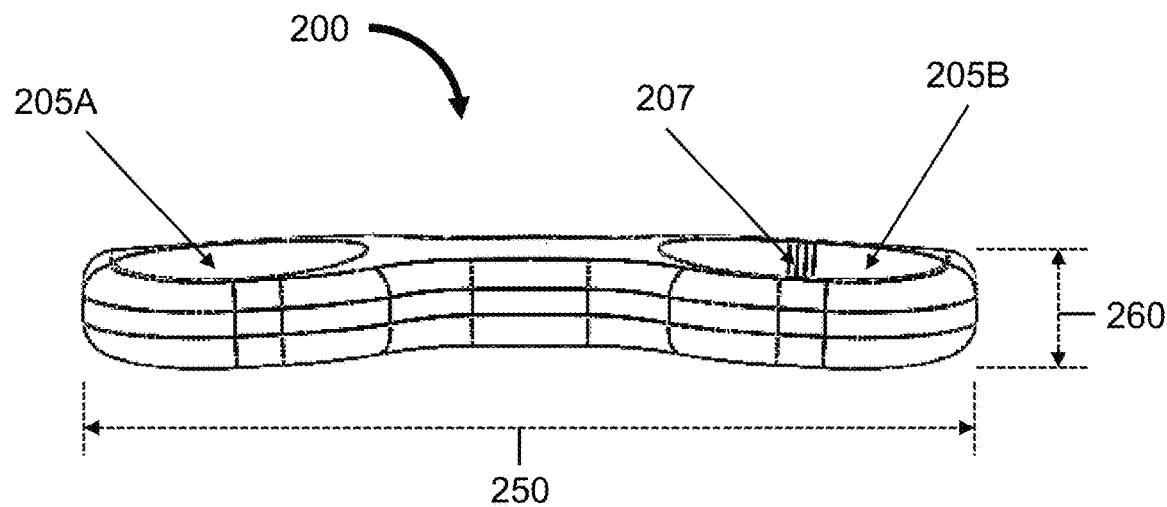
FIGS. 5A-5C are different views of a bone plate according to embodiments of the present invention.
Figure 5B:
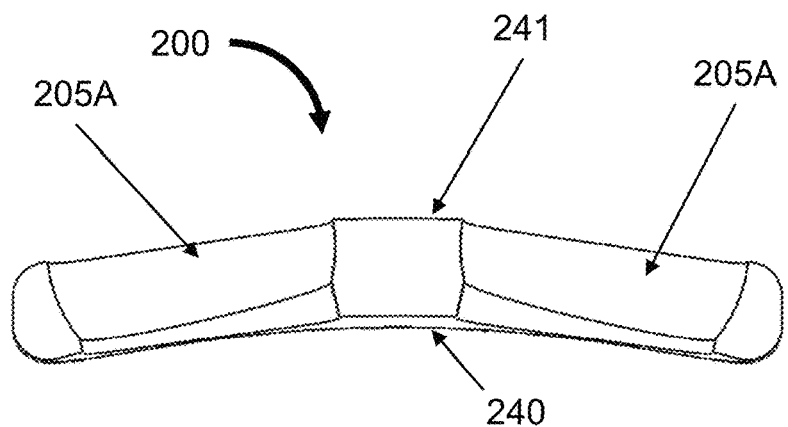
Figure 5C:
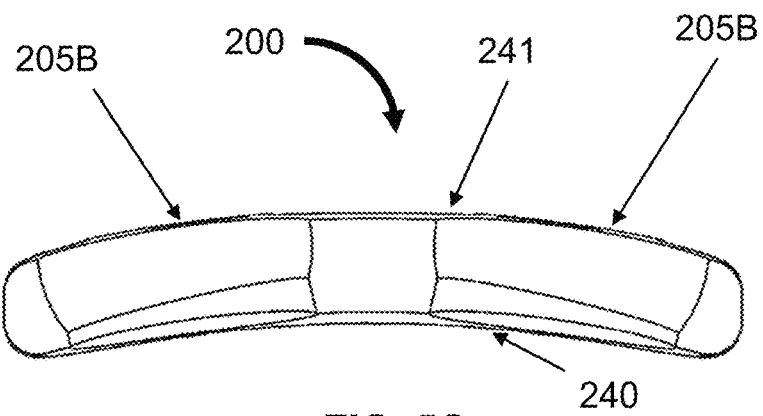
Figure 6:
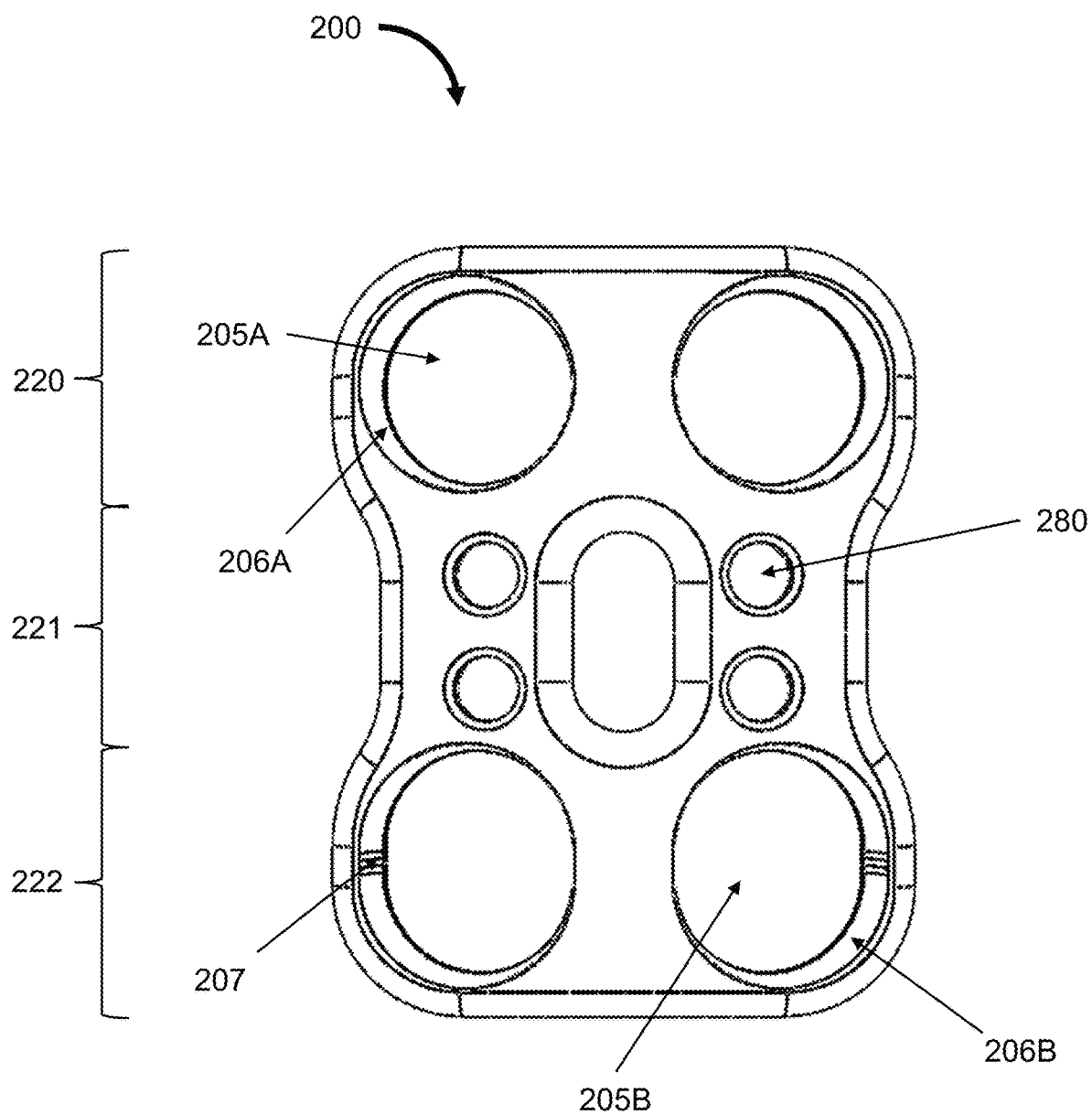
FIG. 6 is a top view of a bone plate according to embodiments of the present invention.

The middle section 221 may comprise one or more apertures (not shown). In certain embodiments, the number of apertures in the middle section 221 along the second axis 211 is the same as the number of apertures 205A in the first end section 220 along the second axis 211 and/or the number of apertures 205B in the second end section 222 along the second axis 211. In other words, if the apertures 205A of the first end section 220 and the apertures 205B of the second end section are each considered as "rows" (as shown in FIG. 4), then the middle section may also comprise one or more "rows" of apertures, in which each row (across the first end, middle, and second end sections) have the same number of apertures. In certain embodiments, the apertures in the middle section are in the shape of an elongated slot, similar to apertures 205B of the second end section 222.

The apertures 205A of the first end section 220, the apertures 205B of the second end section 222, and any apertures of the middle section 221 all may be configured to accept a bone screw 100 of the invention. FIGS. 9A, 9B, 10, 11A, and 11B show examples of the bone screw 100 inserted into the apertures.

Figure 12A:
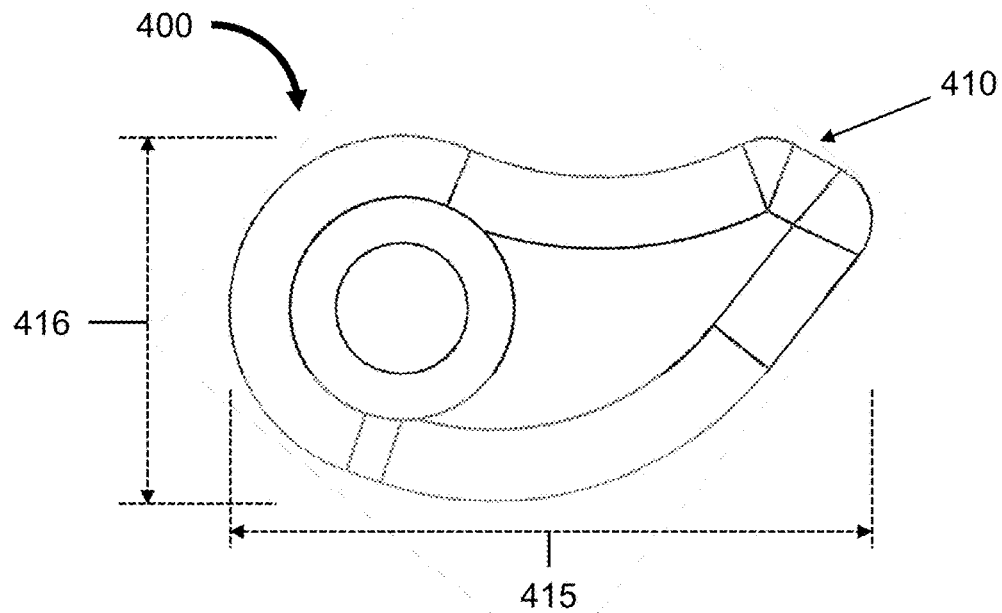
FIGS. 12A and 12B are different views of a locking tab according to embodiments of the present invention.
Figure 12B:
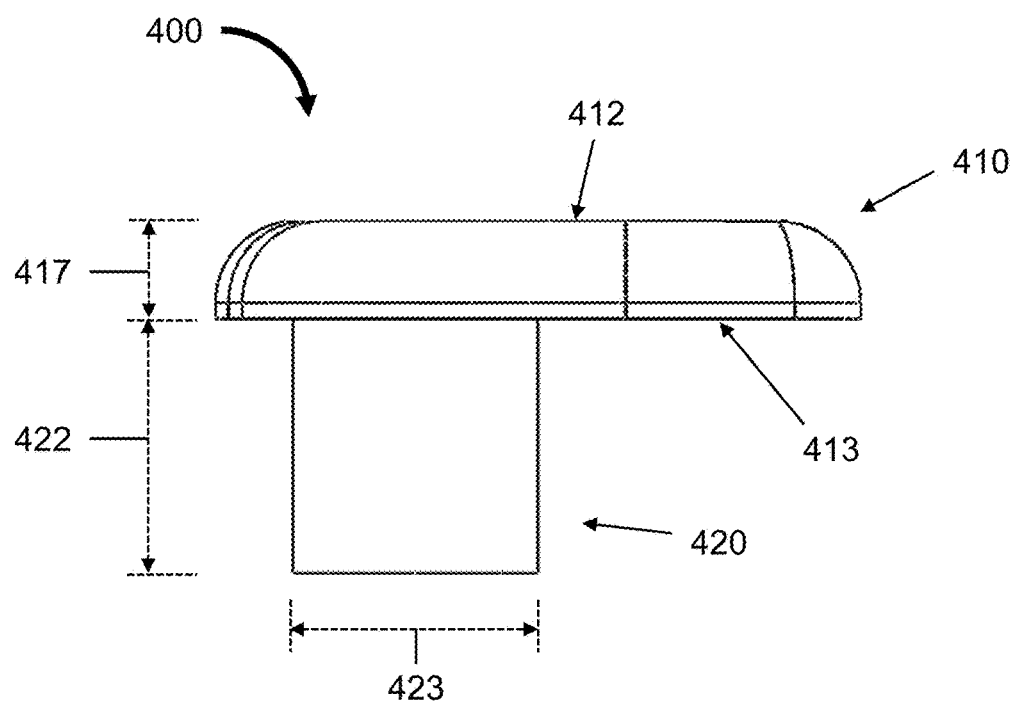

The bone plate 200 may comprise one or more bores 280 that are configured to engage with a locking tab. The locking tab can prevent a bone screw 100 from backing out of the bone once the screw 100 has been inserted into bone through the aperture. An example of a locking tab is shown in FIGS. 12A and 12B. The locking tab 400 may comprise a head 410 and a stem 420. The head 410 may comprise a top surface 412 and a bottom surface 413, in which the bottom surface 413 is relatively flat. The head 410 may be of any shape, including irregular shapes such as the head 410 shown in FIG. 12A, which resembles a tear drop. The size of the head 410 (for example, length 415 and width 416) is limited by the size of the bone plate 200. For example, the head 410 may be large enough to extend from the bore 280 that will engage with the locking tab 400, to the bone screw 100 that is inserted through an aperture of the bone plate 200. But the head 410 may not extend beyond the edges of the bone plate 200. The thickness 417 of the head 410 may be about 1 to about 10 mm, or about 3 to about 8 mm. The stem 420 is generally cylindrical in shape and is configured to engage with, or be inserted into, the bore 280 of the bone plate 200. The length 422 of the stem 420 is no greater than the thickness 260 of the bone plate 200, and the diameter 423 of the stem 420 is configured to the size of the bore 280.

The bone plate 200 may be generally square or rectangular in shape. In some embodiments, the plate 200 may comprise a generally rounded square or a generally rounded rectangle, i.e., has rounded corners.

In certain embodiments, the plate 200 may comprise edges that are fillet 202. For example, the fillet may comprise a radius of about 0.5 to about 1 mm, such as about 0.75 mm.

The bone plate 200 may comprise a vertebra-facing surface 240 and an outward-facing surface 241 (i.e., non-vertebra-facing surface). The vertebra-facing surface 240 may be curved along the first axis 210 (equates to the sagittal anatomic plane) and the second axis 211 (equates to the transverse anatomic plane) to configure to the contouring profile of a vertebral body or a portion thereof, or to configure to the vertebral bodies of one or more adjacent vertebrae or portions thereof, such as cervical or lumbar vertebrae. In certain embodiments, the vertebra-facing surface 240 is generally concave. In some embodiments, the outward-facing surface 241 may also be curved, and may be generally convex.

The bone plate 200 may be comprised of materials known in the art for having orthopedic applications. In certain embodiments, the plate 200 may comprise a uniform material. In some embodiments, the plate 200 may comprise a metal alloy, such as titanium, cobalt-chromium, stainless steel, or a combination thereof. In certain embodiments, the plate 200 may comprise a polymer, such as polyetheretherketone (PEEK) or polyurethane, or a combination thereof. In alternative embodiments, the plate 200 may comprise composites of polymers and fibers, such as carbon fiber-reinforced PEEK.

The plate 200 may comprise a length 250 that is dependent on the number of apertures in the direction of the first axis that is in the middle section 221. For example, if there are no apertures in the middle section 221, the length 250 of the plate 200 may be about 10 to 50 mm. If there is one "row" of one or more apertures in the middle section, i.e., at least one aperture along the first axis 210 in the middle section 221, then the length 250 of the plate 200 may be about 30 mm to about 60 mm. If there are two "rows" of one or more apertures in the middle section 221, i.e., two apertures along the first axis 210, then the length 250 of the plate 200 may be about 45 mm to about 90 mm. The length 250 of the plate 200 is proportionally longer if there are three "rows" of apertures, four "rows" of apertures, etc.

The width 255A of the first end section 220 and the second end section 222 of the plate 200 may be the same. The width 255A may be about 12 mm to about 20 mm for applications relating to cervical vertebrae, and about 8 mm to about 20 mm for applications relating to thoracic/lumbar vertebrae. In certain embodiments, the width 255B of the middle section 221 may be the same as the width 255A, such as if the middle section 221 comprises one or more apertures. In some embodiments, the width 255B of the middle section 221 may be less than the width 255A of the first section 220 or the second section 222, such as if the middle section 221 does not comprise any apertures; in these embodiments, the width 255B of the middle section may be about 10 mm to about 18 mm for applications relating to cervical vertebrae, or about 8 mm to about 20 mm for applications relating to thoracic/lumbar vertebrae.

The thickness 260 of the plate 200 may vary according to the type of vertebrae in which the plate 200 will be attached. For example, for attachment to the vertebral bodies of cervical vertebrae, the thickness 260 may be about 1 mm to about 5 mm; for attachment to the vertebral bodies of thoracic or lumbar vertebrae, the thickness 260 may be about 1 mm to about 6 mm.

The size of the apertures may accommodate the bone screws 100 of the present invention. For example, the diameter 230 of the aperture 205A may be about 4 to about 6 mm for a plate 200 that will be attached to the vertebral bodies of cervical vertebrae, and about 4.5 to about 9.5 mm for a plate 200 that will be attached to the vertebral bodies of thoracic/lumbar vertebrae. The width 232 (measured in the direction of the second axis 211 of the plate 200) of the aperture 205B may be about 4 to about 6 mm for a plate 200 that will be attached to the vertebral bodies of cervical vertebrae, and about 4.5 to about 9.5 mm for a plate 200 that will be attached to the vertebral bodies of thoracic/lumbar vertebrae. The length 231 (measured in the direction of the first axis of the plate 200) of the aperture 205B may be about 5 to about 7 mm for a plate 200 that will be attached to the vertebral bodies of cervical vertebrae, and about 5 to about 11 mm for a plate 200 that will be attached to the vertebral bodies of thoracic/lumbar vertebrae.

Methods of Use of the Bone Screws and Bone Plate

The bone screws and bone plate of the present invention may be used to stabilize and provide compression to an intervertebral joint undergoing fusion. In certain embodiments, the bone screws and bone plate of the present invention may be used to prevent or retard the deterioration of one or more nonfused intervertebral joints that are adjacent to the fused intervertebral joint.

"Fused intervertebral joint" refers to a joint between two vertebrae that is permanently connected, which eliminates the motion between the vertebrae. Fusion may occur by surgical methods known in the art, for example, through bone grafting—from the patient or donor, or with artificial bone substitutes—often with associated stabilizing implants such as plates and screws or rods and screws to help the vertebrae heal together. "Nonfused intervertebral joint" refers to a joint between two vertebrae that is not surgically connected or have not spontaneously fused.

"Deterioration" in this context refers to destruction of tissues within the intervertebral joint between two vertebrae including cartilage, annulus and disc nucleus materials. Deterioration may occur from the transfer of additional loads to a nonfused intervertebral joint that is above (i.e., superior) or below (i.e., inferior) the fused intervertebral joint. In particular, the loading may cause the adjacent nonfused intervertebral joint to compress, such that the vertebrae forming the joint are being pulled toward each other. Without being bound by theory, the present invention prevents and/or reduces deterioration by preventing or reducing the additional loading that is causing the nonfused intervertebral joint to compress.

Therefore, an aspect of the invention is directed to a method of stabilizing or providing compression at a fused intervertebral joint or at an intervertebral joint undergoing fusion. In embodiments of the invention, the method may comprise fastening a bone plate of the invention to the first vertebra and the second vertebra that form the fused/fusing intervertebral joint, such that the bone plate bridges the intervertebral joint. The bone plate may be fastened by inserting a bone screw of the invention through each of the apertures of the bone plate and into the vertebra. The bone plate may be fastened to the vertebral bodies of the first and second vertebrae. The bone plate may be fastened such that the vertebra-facing surface of the bone plate is against the vertebral bodies.

A scope may be used to monitor the placement of the bone plate and the fastening of the screws. In some embodiments, intraoperative fluoroscopy is used.

FIGS. 13A, 13B, 14A, and 14B illustrate the bone plate 200 fastened via one or more bone screws 100 to the vertebral body 310A of a first vertebra 300A and to the vertebral body 310B of a second vertebra 300B, according to certain embodiments of the invention. The intervertebral joint 320 between the first vertebra 300A and the second vertebra 300B may be fused or undergoing fusion. Bone screw(s) 100 may be inserted into aperture(s) 205A of the first end section 220 to fasten the bone plate 200 to the vertebral body 310A of the first vertebra 300A, and bone screw(s) 100 may be inserted into aperture(s) 205B of the second end section 222 to fasten the bone plate 200 to the vertebral body 310B of the second vertebra 300B. The bone plate may be positioned such that the vertebra-facing surface 240 of the bone plate is against the vertebral body 310A of the first vertebra 300A and against the vertebral body 310B of the first vertebra 300B. In certain embodiments, bone screw(s) 100 may be inserted into aperture(s) 205A of the first end section 220 to fasten the bone plate 200 to the vertebral body 310B of the second vertebra 300B, and bone screw(s) 100 may be inserted into aperture(s) 205B of the second end section 222 to fasten the bone plate 200 to the vertebral body 310A of the first vertebra 300A (not shown).

In certain embodiments, the bone screws used to fasten the bone plate to the vertebral body of the first vertebra and the vertebral body of the second vertebra may be oriented so that the polarity of the magnets within the bone screws generate a magnetic attraction between the bone screw(s) inserted into the vertebral body of the first vertebra and the bone screw(s) inserted into the vertebral body of the second vertebra. An example of such embodiments is illustrated in FIGS. 13A, 14A, and 15, in which the mark 145 on the bone screws 100 may be used to determine how to orient the screws 100 so that the bone screw(s) 100 in the aperture(s) 205A and the bone screw(s) 100 in the aperture(s) 205B are subject to an attractive force. These attractive forces between the bone screw(s) 100 in the aperture(s) 205A and the bone screw(s) 100 in the aperture(s) 205B may provide stability and/or provide compression at the fused/fusing intervertebral joint 320. In some embodiments, due to the forces of magnetic attraction, the bone screw(s) 100 can move within the aperture(s) 205B, which are shaped as elongated slots as shown in FIGS. 13A, 14A, and 15. Such movement can bring the bone screw(s) 100 in aperture(s) 205A and the bone screw(s) 100 in the aperture(s) 205B toward each other, thereby causing the first vertebra 300A and the second vertebra 300B to move towards each other. Such movement may also provide stability and/or provide compression at the fused/fusing intervertebral joint.

An aspect of the invention relates to a method of stabilizing fused intervertebral joints between three or more vertebrae (not shown). In embodiments of the invention, the method may comprise fastening a bone plate of the invention to each of the three or more vertebrae that form the fused/fusing intervertebral joints, such that the bone plate bridges the intervertebral joints. The bone plate may be fastened by inserting a bone screw of the invention through each of the apertures of the bone plate and into each of the vertebra. The bone plate may be fastened to the vertebral bodies of each vertebra. The bone plate may be fastened such that the vertebra-facing surface of the bone plate is against the vertebral bodies. For these methods, the bone plate may comprise a middle section that contains one or more rows of apertures. In certain embodiments, bone screws inserted through apertures of the first end section may be fastened to the superior-most vertebra, bone screws inserted through apertures of the second end section may be fastened to the inferior-most vertebra, and bone screws inserted through apertures of the middle section may be fastened to vertebrae therebetween. Alternatively, bone screws inserted through apertures of the first end section may be fastened to the inferior-most vertebra, bone screws inserted through apertures of the second end section may be fastened to the superior-most vertebra, and bone screws inserted through apertures of the middle section may be fastened to vertebrae therebetween.

Another aspect of the invention is directed to a method of preventing or reducing deterioration of a nonfused intervertebral joint that is superior or inferior to a fused/fusing intervertebral joint. The method may comprise inserting one or more bone screws of the invention into a vertebral body of a first vertebra that forms part of the fused/fusing intervertebral joint, and inserting one or more bone screws of the invention into a vertebral body of an adjacent vertebra that does not form the fused/fusing intervertebral joint, such that the first vertebrae and the adjacent vertebrae form a nonfused intervertebral joint. The bone screws may be oriented so that their polarity generates a repulsive force between the bone screw(s) inserted into the first vertebra and the bone screw(s) inserted into the adjacent vertebra. Such a repulsive force prevents or reduces loading that may be caused by the presence of the fused intervertebral joint. An example of embodiments of the invention is illustrated in FIGS. 16A, 16B, and 17, in which first vertebra 300A and second vertebra 300B form a fused/fusing intervertebral joint 320; vertebra 300C forms a nonfused intervertebral joint 330 with vertebra 300A; and vertebra 300D forms a nonfused intervertebral joint 330 with vertebra 300B. Bone screws 100 are inserted into each of vertebral bodies 310A, 310B, 310C, and 310D of vertebrae 300A, 300B, 300C, and 300D, respectively. The marks 145 are used to orient the bone screws 100 such that the polarities of the magnets within the bone screws 100 generate an attractive force between the bone screws fastened to vertebrae 300A and 300B (vertebrae between which there is a fused/fusing intervertebral joint 320), a repulsive force between the bone screws 100 fastened to vertebrae 300A and 300C (vertebrae between which there is a nonfused intervertebral joint 330), and a repulsive force between the bone screws 100 fastened to vertebrae 300B and 300D (vertebrae between which there is a nonfused intervertebral joint 330) (see FIG. 17). The repulsive forces can help prevent degeneration at the nonfused intervertebral joints.

In some embodiments, bone screw(s) may be inserted into a vertebral body of one or more vertebrae superior or inferior to vertebrae of a fused/fusing intervertebral joint that are fastened with a bone plate. An example of such embodiments is illustrated in FIGS. 18A, 18B, and 19. A bone plate 200 may be fastened via bone screws 100 to a vertebral body 310A of a vertebra 300A and to a vertebral body 310B of a vertebra 300B, such that the bone plate 200 bridges a fused/fusing intervertebral joint 320 between vertebra 300A and vertebra 300B. Bone screws 100 may be inserted into a vertebral body 310C of a third vertebra 300C superior to the first vertebra 300A, in which a nonfused intervertebral joint 330 is between the first vertebra 300A and the third vertebra 300C; and bone screws 100 may be inserted into a vertebral body 310D of a fourth vertebra 300D inferior to the second vertebra 300B, in which a nonfused intervertebral joint 330 is between the second vertebra 300B and the fourth vertebra 300D. Guided by the marks 145, the bone screws 100 may be oriented so that the polarity of the magnets within the bone screws 100 generate attractive and repulsive forces among the bone screws. As illustrated in FIG. 19, the bone screws 100 may be oriented so that an attractive force is generated between the bone screws 100 inserted into the first vertebra 300A and the bone screws 100 inserted into the second vertebra 300B. In addition, a repulsive force is generated between the bone screws 100 inserted into the first vertebra 300A and the bone screws 100 inserted into the third vertebra 300C. Further, a repulsive force is generated between the bone screws 100 inserted into the second vertebra 300B and the bone screws 100 inserted into the fourth vertebra 300D.

An additional aspect of the invention relates to using the bone screws and/or bone plate of the invention to promote bone healing. In some embodiments, one or more bone screws may be inserted into each side of a bone fracture or break. The bone screws may be oriented to generate a magnetic attractive force between the one or more bone screws on one side of the fracture/break, and the one or more screws on the other side of the fracture/break.

In certain embodiments, the bone plate of the invention may be fastened to the fractured/broken bone, such that the plate bridges the fracture/break. Bone screws of the invention may be used to fasten the plate to the bone, and may be oriented to generate a magnetic attractive force between the bone screw(s) that fasten the bone plate to one side of the fracture/break, and the bone screw(s) that fasten the bone plate to the other side of the fracture/break.

The bone screws and/or bone plate of the invention may be used to promote healing in various types of bones, including long bones (e.g., humerus, radius, ulna, femur, tibia, fibula, etc.), short bones (e.g., metacarpals, phalanges, metatarsals, etc.), flat bones (e.g., scapula, ribs, sternum, etc.), and irregular bones (e.g., vertebrae, carpal bones, tarsal bones, etc.).

The foregoing description is given for clearness of understanding only, and no unnecessary limitations should be understood therefrom, as modifications within the scope of the invention may be apparent to those having ordinary skill in the art.

Detailed embodiments of the present bone screw, plate, plate-and-screw apparatus, and methods thereof are disclosed herein; however, it is to be understood that the disclosed embodiments are merely illustrative of the bone screw, plate, plate-and-screw apparatus, and method that may be embodied in various forms. In addition, each of the examples given in connection with the various embodiments of the systems and methods are intended to be illustrative, and not restrictive.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A bone screw comprising
   (a) a shaft comprising:
      (i) a head, a lower section, and a middle section therebetween, wherein the shaft comprises a circular cross-section;
      (ii) an outer wall surface, wherein a plurality of threads is disposed along at least a portion of the outer wall surface; and
      (iii) a bore defining an inner wall surface and located in the middle section, wherein the bore comprises a substantially cylindrical shape containing a flattened side in the direction of the long axis of the bore; and
   (b) a magnet configured to fit within the bore, wherein the magnet is a rare-earth magnet and comprises a substantially cylindrical shape containing a flattened side in the direction of the long axis of the magnet.

2. The bone screw of claim 1, wherein the lower section of the shaft is attached to the middle section.

3. The bone screw of claim 2, wherein the lower section is hermetically sealed to the middle section.

4. The bone screw of claim 1, wherein the upper section head of the shaft comprises an end surface that is configured to receive a driver.

5. A method of preventing or reducing deterioration of a nonfused intervertebral joint of a first vertebra and a second vertebra that is superior or inferior to a fused/fusing intervertebral joint, comprising inserting at least one bone screw according to claim 1 into each of the first vertebra and the second vertebra,
   wherein the at least one bone screw inserted into each of the first vertebra and the second vertebra are oriented to generate an attractive magnetic force between the at least one bone screw inserted into the first vertebra and the at least one bone screw inserted into the second vertebra.

6. A bone screw comprising
   (a) a shaft comprising:
      (i) a head, a lower section, and a middle section therebetween, wherein the shaft comprises a circular cross-section;
      (ii) an outer wall surface, wherein a plurality of threads is disposed along at least a portion of the outer wall surface; and
      (iii) a bore defining an inner wall surface; and
   (b) a magnet configured to fit within the bore, wherein the magnet is a rare-earth magnet;
   wherein the head of the shaft comprises an end surface that is configured to receive a driver, and
   wherein the end surface of the head contains a mark that identifies the polarity of the magnet.

7. The bone screw of claim 6, wherein the lower section of the shaft is attached to the middle section.

8. The bone screw of claim 7, wherein the lower section is hermetically sealed to the middle section.

9. An apparatus comprising:
   (1) plate comprising a first end section, a second end section, and a middle section therebetween; and a first surface and a second surface; wherein
      (a) the first end section comprises one or more apertures, wherein the one or more apertures of the first end section is substantially circular;
      (b) the second end section comprises one or more apertures, wherein the one or more apertures of the second end section is substantially an elongated slot; and
      (c) the first surface comprises a contouring profile configured to the contouring profile of adjacent vertebrae; and
   (2) at least two bone screws, wherein each of the two bone screws comprises
      (a) a shaft comprising:
         (i) a head, a lower section, and a middle section therebetween, wherein the shaft comprises a circular cross-section;
         (ii) an outer wall surface, wherein a plurality of threads are disposed along at least a portion of the outer wall surface; and (iii) a bore defining an inner wall surface and located in the middle section, wherein the bore comprises a substantially cylindrical shape containing a flattened side in the direction of the long axis of the bore; and
(b) a magnet configured to fit within the bore, wherein the magnet is a rare-earth magnet and comprises a substantially cylindrical shape containing a flattened side in the direction of the long axis of the magnet;
wherein the at least one aperture one or more apertures of the first end section and the one or more apertures of the second section are each configured to receive one of the at least two bone screws.

10. The apparatus of claim 9, wherein the first surface comprises a contouring profile configured to the contouring profile of vertebral bodies of adjacent vertebrae.

11. The apparatus of claim 9, wherein two apertures are in the first end section and two apertures are in the second end section.

12. The apparatus of claim 9, wherein the lower section is attached to the middle section.

13. The apparatus of claim 12, wherein the lower section is hermetically sealed to the middle section.

14. The apparatus of claim 9, wherein the head comprises an end surface that is configured to receive a driver.

15. The apparatus of claim 9, wherein the head comprises an end surface containing a mark that identifies the polarity of the magnet.

16. A method of preventing or reducing deterioration of a nonfused intervertebral joint of a first vertebra and a second vertebra that is superior or inferior to a fused/fusing intervertebral joint, comprising inserting at least one bone screw according to claim 9 into each of the first vertebra and the second vertebra,
wherein the at least one bone screw inserted into each of the first vertebra and the second vertebra are oriented to generate an attractive magnetic force between the at least one bone screw inserted into the first vertebra and the at least one bone screw inserted into the second vertebra.

17. The apparatus of claim 9, wherein the one or more apertures of the first end section of the plate is circular.

18. The apparatus of claim 9, wherein the one or more apertures of the second end section of the plate is an elongated slot.

19. The apparatus of claim 9, wherein the first end section of the plate comprises no more than two apertures, and the second end section of the plate comprises no more than two apertures.

20. A method of stabilizing a fused intervertebral joint between a first vertebra and a second vertebra, comprising fastening a bone plate via one or more bone screws to the first vertebra and the second vertebra, wherein the plate traverses the fused intervertebral joint;
wherein the plate comprising a first end section, a second end section, and a middle section therebetween; and a first surface and a second surface; wherein
(a) the first end section comprises one or more apertures, wherein the one or more apertures of the first end section is substantially circular;
(b) the second end section comprises one or more apertures, wherein the one or more apertures of the second end section is substantially an elongated slot; and
(c) the first surface comprises a contouring profile configured to the contouring profile of adjacent vertebrae; and wherein each of the two or more bone screws comprises
(a) a shaft comprising:
(i) a head, a lower section, and a middle section therebetween, wherein the shaft comprises a circular cross-section;
(ii) an outer wall surface, wherein a plurality of threads is disposed along at least a portion of the outer wall surface; and
(iii) a bore defining an inner wall surface and located in the middle section, wherein the bore comprises a substantially cylindrical shape containing a flattened side in the direction of the long axis of the bore; and
(b) a magnet configured to fit within the bore, wherein the magnet is a rare-earth magnet and comprises a substantially cylindrical shape containing a flattened side in the direction of the long axis of the magnet, and wherein the magnet generates a magnetic force; and
wherein the two or more bone screws are inserted through the apertures of the plate to fasten the plate to the first vertebra and the second vertebra, wherein at least one of the two or more bone screws is inserted through the one or more apertures of the first end section to fasten the first end section to the first vertebra, and at least one of the two or more bone screws is inserted though the one or more apertures of the second end section to fasten the second end to the second vertebra; and
wherein the two or more bone screws are oriented to generate an attractive magnetic force between the at least one of the two or more bone screws inserted through the one or more apertures of the first end section and the at least one of the two or more bone screws inserted though the one or more apertures of the second end section.

21. The method of claim 20, wherein the one or more apertures of the first end section of the plate is circular.

22. The method of claim 20, wherein the one or more apertures of the second end section of the plate is an elongated slot.

23. The method of claim 20, wherein the first end section of the plate comprises no more than two apertures, and the second end section of the plate comprises no more than two apertures.

24. An apparatus comprising:
(1) plate comprising a first end section, a second end section, and a middle section therebetween; and a first surface and a second surf ace; wherein
(a) the first end section comprises one or more apertures, wherein the one or more apertures of the first end section is substantially circular;
(b) the second end section comprises one or more apertures, wherein the one or more apertures of the second end section is substantially an elongated slot; and
(c) the first surface comprises a contouring profile configured to the contouring profile of adjacent vertebrae; and
(2) at least two bone screws, wherein each of the two bone screws comprises
(a) a shaft comprising:
(i) a head, a lower section, and a middle section therebetween, wherein the shaft comprises a circular cross-section;
(ii) an outer wall surface, wherein a plurality of threads are disposed along at least a portion of the outer wall surface; and (iii) a bore defining an inner wall surface; and
(b) a magnet configured to fit within the bore, wherein the magnet is a rare-earth magnet;
wherein the head of the shaft comprises an end surface that is configured to receive a driver, and
wherein the end surface of the head contains a mark that identifies the polarity of the magnet;
wherein the one or more apertures of the first end section and the one or more apertures of the second section are each configured to receive one of the at least two bone screws.

25. The apparatus of claim 24, wherein the first surface comprises a contouring profile configured to the contouring profile of vertebral bodies of adjacent vertebrae.

26. The apparatus of claim 24, wherein two apertures are in the first end section and two apertures are in the second end section.

27. The apparatus of claim 24, wherein the lower section is attached to the middle section.

28. The apparatus of claim 27, wherein the lower section is hermetically sealed to the middle section.

29. The apparatus of claim 24, wherein the one or more apertures of the first end section of the plate is circular.

30. The apparatus of claim 24, wherein the one or more apertures of the second end section of the plate is an elongated slot.

31. The apparatus of claim 24, wherein the first end section of the plate comprises no more than two apertures, and the second end section of the plate comprises no more than two apertures.

32. A method of stabilizing a fused intervertebral joint between a first vertebra and a second vertebra, comprising fastening a bone plate via two or more bone screws to the first vertebra and the second vertebra, wherein the plate traverses the fused intervertebral joint;
wherein the plate comprising a first end section, a second end section, and a middle section therebetween; and a first surface and a second surface; wherein
(a) the first end section comprises one or more apertures, wherein the one or more apertures of the first end section is substantially circular;
(b) the second end section comprises one or more apertures, wherein the one or more apertures of the second end section is substantially an elongated slot; and
(c) the first surface comprises a contouring profile configured to the contouring profile of adjacent vertebrae; and
wherein each of the two or more bone screws comprises
(a) a shaft comprising:
(i) a head, a lower section, and a middle section therebetween, wherein the shaft comprises a circular cross-section;
(ii) an outer wall surface, wherein a plurality of threads is disposed along at least a portion of the outer wall surface; and
(iii) a bore defining an inner wall surface; and
(b) a magnet configured to fit within the bore, wherein the magnet is a rare-earth magnet, and wherein the magnet generates a magnetic force
wherein the head of the shaft comprises an end surface that is configured to receive a driver, and
wherein the end surface of the head contains a mark that identifies the polarity of the magnet; and
wherein the two or more bone screws are inserted through the apertures of the plate to fasten the plate to the first vertebra and the second vertebra, wherein at least one of the two or more bone screws is inserted through the one or more apertures of the first end section to fasten the first end section to the first vertebra, and at least one of the two or more bone screws is inserted though the one or more apertures of the second end section to fasten the second end to the second vertebra; and
wherein the two or more bone screws are oriented to generate an attractive magnetic force between the at least one of the two or more bone screws inserted through the one or more apertures of the first end section and the at least one of the two or more bone screws inserted though the one or more apertures of the second end section.

33. The method of claim 32, wherein the one or more apertures of the first end section of the plate is circular.

34. The method of claim 32, wherein the one or more apertures of the second end section of the plate is an elongated slot.

35. The method of claim 32, wherein the first end section of the plate comprises no more than two apertures, and the second end section of the plate comprises no more than two apertures.

* * * * *